(12) United States Patent
Alt et al.

(10) Patent No.: US 11,497,862 B2
(45) Date of Patent: Nov. 15, 2022

(54) INTRANASAL DRUG DELIVERY DEVICE, SYSTEM, AND PROCESS

(71) Applicant: Rocket Science Health Corp., Victoria (CA)

(72) Inventors: David James Alt, North Vancouver (CA); Kenneth Colin MacNarin Irving, Victoria (CA); James Patrick Jackson, Victoria (CA); Peter Oxley, Rothesay (CA); Kenza Elizabeth Coubrough, Seattle, WA (US)

(73) Assignee: Rocket Science Health Corp., Victoria (CA)

( * ) Notice: Subject to any disclaimer, the term of this patent is extended or adjusted under 35 U.S.C. 154(b) by 0 days.

(21) Appl. No.: 16/944,080

(22) Filed: Jul. 30, 2020

(65) Prior Publication Data

US 2020/0353183 A1 Nov. 12, 2020

Related U.S. Application Data

(63) Continuation of application No. PCT/CA2019/050455, filed on Apr. 12, 2019.
(Continued)

(51) Int. Cl.
*A61M 11/00* (2006.01)
*A61M 15/00* (2006.01)
*A61M 15/08* (2006.01)

(52) U.S. Cl.
CPC ...... *A61M 11/007* (2014.02); *A61M 15/0036* (2014.02); *A61M 15/08* (2013.01);
(Continued)

(58) Field of Classification Search
CPC .. A61M 11/007; A61M 11/006; A61M 15/08; A61M 15/0036; A61M 2210/0058
See application file for complete search history.

(56) References Cited

U.S. PATENT DOCUMENTS

| 729,566 A | 6/1903 | Foglesong |
| 1,044,145 A | 11/1912 | Cruser |

(Continued)

FOREIGN PATENT DOCUMENTS

| CA | 2256008 A1 | 12/1997 |
| CA | 2792676 A1 | 9/2011 |

(Continued)

OTHER PUBLICATIONS

Abreu et al.: Sinus microbiome diversity depletion and Corynebacterium tuberculostearicum enrichment mediates rhinosinusitis. Sci Transl Med. 4:151ra124 (2012) https://doi.org/10.1126/scitranslmed.3003783.
(Continued)

*Primary Examiner* — Nathan R Price
*Assistant Examiner* — Courtney B Fredrickson
(74) *Attorney, Agent, or Firm* — Wilson Sonsini Goodrich & Rosati

(57) ABSTRACT

Embodiments relate to an intranasal drug delivery device, system, and process. The drug delivery device can have a compliant/flexible soft nib. The drug delivery device can have an actuator and shot chamber. The drug delivery device can have a non-air interface mechanically pressurized fluid reservoir. The drug delivery device can have a facial or device recognition application to prevent intentional or unintentional misuse.

12 Claims, 30 Drawing Sheets

Related U.S. Application Data

(60) Provisional application No. 62/774,444, filed on Dec. 3, 2018, provisional application No. 62/656,463, filed on Apr. 12, 2018.

(52) U.S. Cl.
CPC ... *A61M 2205/52* (2013.01); *A61M 2205/609* (2013.01); *A61M 2205/8281* (2013.01); *A61M 2206/11* (2013.01); *A61M 2210/0618* (2013.01)

(56) References Cited

U.S. PATENT DOCUMENTS

| | | | |
|---|---|---|---|
| 4,335,756 A | 6/1982 | Sharp et al. | |
| 5,092,845 A | 3/1992 | Chang | |
| 5,224,471 A | 7/1993 | Marelli et al. | |
| 5,291,897 A | 3/1994 | Gastrin et al. | |
| 5,307,953 A | 5/1994 | Regan | |
| 5,331,954 A | 7/1994 | Rex et al. | |
| 5,419,766 A | 5/1995 | Chang et al. | |
| 5,540,666 A | 7/1996 | Barta et al. | |
| 5,599,310 A | 2/1997 | Bogert | |
| 5,670,558 A | 9/1997 | Onishi et al. | |
| 6,112,743 A | 9/2000 | Denton | |
| 6,180,603 B1 | 1/2001 | Frey, II | |
| 6,293,927 B1 | 9/2001 | McGuckin, Jr. | |
| 6,382,465 B1* | 5/2002 | Greiner-Perth ... | A61M 15/0065 222/309 |
| 6,383,191 B1 | 5/2002 | Zdeblick et al. | |
| 6,416,522 B1 | 7/2002 | Strecker | |
| 6,536,437 B1 | 3/2003 | Dragisic | |
| 7,039,450 B2 | 5/2006 | Duarte | |
| 7,094,220 B2 | 8/2006 | Tanghoj et al. | |
| 7,195,615 B2 | 3/2007 | Tan | |
| 7,258,119 B2* | 8/2007 | Mazzoni ........... | A61M 15/0028 128/200.14 |
| 7,296,566 B2 | 11/2007 | Alchas | |
| 7,311,698 B2 | 12/2007 | Tanghoj et al. | |
| 7,762,995 B2 | 7/2010 | Eversull et al. | |
| 7,770,726 B2 | 8/2010 | Murray et al. | |
| 7,799,337 B2 | 9/2010 | Levin | |
| 7,918,831 B2 | 4/2011 | House | |
| 8,001,963 B2 | 8/2011 | Giroux | |
| 8,066,756 B2 | 11/2011 | Rasmussen et al. | |
| 8,834,513 B2 | 9/2014 | Hanson et al. | |
| 9,011,320 B2 | 4/2015 | Weitzner et al. | |
| 9,168,354 B2 | 10/2015 | Hannon et al. | |
| 9,283,360 B2 | 3/2016 | Lesch et al. | |
| D759,813 S | 6/2016 | Newman et al. | |
| 9,480,644 B2 | 11/2016 | Crystal et al. | |
| 9,550,036 B2* | 1/2017 | Hoekman ........... | A61P 43/00 |
| 9,649,472 B2 | 5/2017 | Kearns et al. | |
| 9,707,226 B2 | 7/2017 | Keegan et al. | |
| 9,821,144 B2 | 11/2017 | Mouri et al. | |
| 9,833,349 B2 | 12/2017 | Dorn | |
| 9,867,907 B2 | 1/2018 | Rostami et al. | |
| 9,918,869 B2 | 3/2018 | Henry et al. | |
| 9,919,117 B2 | 3/2018 | Hoekman et al. | |
| 9,987,464 B1 | 6/2018 | Donald et al. | |
| 10,166,351 B2 | 1/2019 | Eldredge et al. | |
| 10,166,366 B2 | 1/2019 | Murray et al. | |
| 10,327,896 B2 | 6/2019 | Zhou et al. | |
| 10,350,381 B2 | 7/2019 | Schertiger et al. | |
| 2002/0017294 A1 | 2/2002 | Py | |
| 2002/0023641 A1 | 2/2002 | Stadelhofer | |
| 2002/0072712 A1 | 6/2002 | Nool et al. | |
| 2002/0193863 A1 | 12/2002 | Rourke et al. | |
| 2003/0073958 A1* | 4/2003 | Pond ............... | A61M 5/24 604/232 |
| 2004/0153033 A1 | 8/2004 | Mazzoni | |
| 2005/0004553 A1 | 1/2005 | Douk | |
| 2005/0072430 A1* | 4/2005 | Djupesland ........... | A61M 15/08 128/206.11 |
| 2005/0137448 A1 | 6/2005 | Wingler et al. | |
| 2005/0205446 A1 | 9/2005 | Duffy et al. | |
| 2005/0258273 A1* | 11/2005 | Bruna ............... | A61M 15/0028 239/333 |
| 2005/0281751 A1 | 12/2005 | Levin | |
| 2006/0124778 A1 | 6/2006 | Vendrine et al. | |
| 2007/0186927 A1* | 8/2007 | Djupesland .......... | A61M 15/08 128/203.15 |
| 2007/0199732 A1 | 8/2007 | Schnackenberg | |
| 2008/0172042 A1 | 7/2008 | House | |
| 2011/0088690 A1 | 4/2011 | Djupesland et al. | |
| 2011/0114520 A1 | 5/2011 | Matthison-Hansen | |
| 2011/0132354 A1 | 6/2011 | Flickinger et al. | |
| 2012/0323221 A1* | 12/2012 | Gallo .................. | A61M 3/0279 604/514 |
| 2013/0006226 A1 | 1/2013 | Hong et al. | |
| 2013/0142868 A1 | 6/2013 | Hoekman et al. | |
| 2013/0174849 A1* | 7/2013 | Atkinson ............... | A62B 23/06 128/206.11 |
| 2013/0331916 A1 | 12/2013 | Pile-Spellman et al. | |
| 2014/0083424 A1 | 3/2014 | Hoekman et al. | |
| 2014/0336488 A1 | 11/2014 | Das | |
| 2015/0080785 A1 | 3/2015 | Shantha | |
| 2015/0100042 A1 | 4/2015 | Hoekman et al. | |
| 2015/0165139 A1 | 6/2015 | Hafner | |
| 2015/0343171 A1 | 12/2015 | Hannon | |
| 2016/0036774 A1 | 2/2016 | Chong et al. | |
| 2016/0199599 A1 | 7/2016 | Isaacs et al. | |
| 2016/0263285 A1 | 9/2016 | Rostami et al. | |
| 2016/0310683 A1 | 10/2016 | Djupesland et al. | |
| 2016/0367772 A1 | 12/2016 | Djupesland | |
| 2016/0367774 A1 | 12/2016 | Djupesland et al. | |
| 2017/0072145 A1 | 3/2017 | Hadash et al. | |
| 2017/0151397 A1 | 6/2017 | Djupesland | |
| 2017/0265849 A1 | 9/2017 | Assaf et al. | |
| 2018/0001055 A1 | 1/2018 | Utas et al. | |
| 2018/0071482 A1 | 3/2018 | Fitzpatrick et al. | |
| 2018/0071486 A1 | 3/2018 | O'Flynn | |
| 2018/0256867 A1* | 9/2018 | Levin .................. | A61M 11/007 |
| 2018/0280659 A1 | 10/2018 | Kearns et al. | |
| 2019/0015613 A1* | 1/2019 | Shahaf ................. | B05B 11/061 |
| 2019/0030214 A1 | 1/2019 | Montes De Oca et al. | |
| 2019/0054016 A1 | 2/2019 | Djupesland | |
| 2019/0091424 A1 | 3/2019 | Haruta | |
| 2019/0209746 A1 | 7/2019 | Baker et al. | |
| 2019/0290865 A1 | 9/2019 | Fahey et al. | |
| 2020/0061335 A1 | 2/2020 | Guldager et al. | |
| 2022/0040424 A1 | 2/2022 | Alt et al. | |

FOREIGN PATENT DOCUMENTS

| | | |
|---|---|---|
| GB | 2262138 A | 6/1993 |
| GB | 2435835 A | 9/2007 |
| WO | WO-9704828 A1 | 2/1997 |
| WO | WO-0047256 A1 | 8/2000 |
| WO | WO-03008029 A2 | 1/2003 |
| WO | WO-2005058400 A1 | 6/2005 |
| WO | WO-2007064657 A1 | 6/2007 |
| WO | WO-2013130459 A1 | 9/2013 |
| WO | WO-2013174381 A1 | 11/2013 |
| WO | WO-2014179767 A2 | 11/2014 |
| WO | WO-2014207212 A1 | 12/2014 |
| WO | WO-2015028658 A1 | 3/2015 |
| WO | WO-2015065725 A1 | 5/2015 |
| WO | WO-2016168461 A1 | 10/2016 |
| WO | WO-2017017423 A1 | 2/2017 |
| WO | WO-2019139901 A1 | 7/2019 |
| WO | WO-2019195944 A1 | 10/2019 |
| WO | WO-2019222644 A1 | 11/2019 |
| WO | WO-2020217097 A1 | 10/2020 |
| WO | WO-2021069972 A1 | 4/2021 |

OTHER PUBLICATIONS

Agah et al.: Osteopontin (OPN) as a CSF and blood biomarker for multiple sclerosis: A systematic review and meta-analysis. PLOS One. 13(1) (2018).

(56) References Cited

OTHER PUBLICATIONS

Baseler et al.: Identifying Early Target Cells of Nipah Virus Infection in Syrian Hamsters. PLoS Negl Trap Dis. 10(11):e0005120 (2016).
Bassis et al.: Pynnonen MA. The nasal cavity microbiota of healthy adults. Microbiome. 2:27 (2014).
Belagavi et al.: Cerebrospinal Fluid C Reactive Protein and Adenosine Deaminase in Meningitis in Adults. JAPI. 59:557-559 (2011).
Bernasconi et al.: Beta-trace Protein Quantification for Diagnosis of CSF Leakage Syndrome. White Paper (2017).
Beta-2 Transferrin/Tau Protein: website: http://www.viapath.co.uk/our-tests/beta-2-transferrintau-protein (2017).
Cerebral spinal fluid (CSF) collection: website: https://medlineplus.gov/ency/article/003428.htm (2020).
Coburn et et.: Lung microbiota across age and disease stage in cystic fibrosis. Sci Rep. 5:10241 (2015) https://doi.org/10.1038/srep10241.
Costello et al.: Bacterial community variation in human body habitats across space and time. Science. 326:1694-7 (2009) https://doi.org/10.1126/science.1177486.
Débat et al.: Identification of Human Olfactory Cleft Mucus Proteins Using Proteomic Analysis. Journal of Proteome Research. 6(5):1985-1996 (2007).
De palos et al.: Does the Cerebrospinal Fluid Reflect Altered Redox State But Not Neurotrophic Support Loss in Parkinson's Disease? Antioxidants & Redox Signaling. 23(11):893-898 (2015).
DeLeon et al.: Cerebrospinal fluid clearance in Alzheimer disease measured with dynamic PET. Journal of Nuclear Medicine. 58(9):1471 (2017).
Felgenhauer: Protein size and CSF composition. Klin. Wochenschr. 52(24):1158-64 (1974).
Garcia-Ayllon et al.: Inhibition of γ-Secretase Leads to an Increase in Presenilin-1. J. Neurochemistry. 101:1701-1711 (2007).
Garland et al.: Heme-Hemopexin Scavenging Is Active in the Brain and Associates With Outcome After Subarachnoid Hemorrhage. Stroke. 47(3):872-876 (2016).
Gevers et al.: The treatment-naive microbiome in new-onset Crohn's disease. Cell Host Microbe. 15:382-92 (2014) https://doi.org/10.1016/j.chom.2014.02.005.
Grenham et al.: Brain-gut-microbe communication in health and disease. Front Physiol. 2:94 (2011) https://doi.org/10.3389/fphys.2011.00094.
Guyton et al.: Textbook of medical physiology (11th ed.). Philadelphia: W.B. Saunders, pp. 764-770 (2005).
Hall et al.: CSF biomarkers and clinical progression of Parkinson disease. Neurology. 84(1):57-63 (2015).
Haque et al.: New Insights into the Role of Neuron-Specific Enolase in Neuro-Inflammation, Neurodegeneration, and Neuroprotection. Brain Sci. 8(2):33 (2018).
Hartstra et al.: Insights into the role of the microbiome in obesity and type 2 diabetes. Diabetes Care. 38:159 (2015) https://doi.org/10.2337/dc14-0769.
Hesse et al.: Measurement of apolipoprotein E (apoE) in cerebrospinal fluid. Neurochem Res 25(4):511-7 (2000).
Johnston et al.: Evidence of connections between cerebrospinal fluid and nasal lymphatic vessels in humans, non-human primates and other mammalian species. Cerebrospinal Fluid Res. 1:2 (2004).
Kawakami et al.: A comparative study of nitric oxide, glutathione, and glutathione peroxidase activities in cerebrospinal fluid from children with convulsive diseases/children with aseptic meningitis. Brain Dev. 28(4):243-246 (2006).
Koskinen et al.: The nasal microbiome mirrors and potentially shapes olfactory function. Sci Rep. 8:1-11 (2018).
Kumpitsch et al.: The microbiome of the upper respiratory tract in health and disease. BMC biology. 17:87 (2019) https://doi.org/10.1186/s12915-019-0703-z.
Lee et al.: Fibrinogen gamma-A chain precursor in CSF: A candidate biomarker for Alzheimer's disease. BMC Neurology. 7(1):7-14 (2007).
Lloyd-Price et al.: Strains, functions and dynamics in the expanded Human Microbiome Project. Nature. 550:61 (2017) https://doi.org/10.1038/nature23889.
Maffei et al.: Levels of antimicrobial molecules defensin and lactoferrin are elevated in the cerebrospinal fluid of children with meningitis. Pediatrics. 10(3):987-92 (1999).
Malla et al.: Is Cerebrospinal Fluid C-reactive Protein a Better Tool than Blood C-reactive Protein in Laboratory Diagnosis of Meningitis in Children? Sultan Qaboos Univ Med. 13(1):93-99 (2013).
MEDWATCH: Competitor accuses Coloplast of dragging out court case and infringing patent. website: https://medwatch.dk/Top_picks_in_english/article10429920.ece (2020).
Mukherjee et al.: Sebum and hydration levels in specific regions of human face significantly predict the nature and diversity of facial skin microbiome. Sci. Rep. 6:36062 (2016).
Nishida et al.: A novel ferritin light chain mutation in neuroferritinopathy with an atypical presentation. J Neuro Sci. 342(2):173-177 (2014).
Oh et al.: Traumatic Cerebrospinal Fluid Leak: Diagnosis and Management. Korean J. Neurotrauma. 13(2):63-67 (2017).
Oudart et al.: Tau protein as a possible marker of cerebrospinal fluid leakage in cerebrospinal fluid rhinorrhoea: A pilot study. Biochem Med (Zagreb). 27(3):030703 (2017).
PCT/CA2019/050455 International Search Report and Written Opinion dated Jul. 8, 2019.
Rathbone et al.: Cerebrospinal fluid immunoglobulin light chain ratios predict disease progression in multiple sclerosis. J Neurol Neurosurg Psychiatry. 89:1044-1049 (2018).
Rebuli Me et al.: Novel applications for a noninvasive sampling method of the nasal mucosa. Am J Physiol Lung Cell Mol Physiol. 312(2):L288-L296 (2017).
Sahin-Yilmaz A, Naclerio RM. Anatomy and physiology of the upper airway. Proc Am Thorac Soc. 2011;8:31-9. https://doi.org/10.1513/pats.201007-050RN.
Saladin. Anatomy and Physiology (6th ed.). McGraw Hill. pp. 519-20 (2012).
Schmidt et al.: Elevated levels of cerebrospinal fluid neuron-specific enolase (NSE) in Alzheimer's disease. Neurosci Lett. 570:81-85 (2014).
Senel et al.: Cerebrospinal Fluid Immunoglobulin Kappa Light Chain in Clinically Isolated Syndrome and Multiple Sclerosis. PLOS One. 9(4) (2014).
Shilts et al.: Minimally Invasive sampling method identifies differences in taxonomic richness of nasal microbiomes in young infants associated with mode of delivery. Microb Ecol. 71:233-42 (2016).
Singh et al.: Cerebrospinal-fluid-derived Immunoglobulin G of Different Multiple Sclerosis Patients Shares Mutated Sequences in Complementarity Determining Regions. Mol Cell Proteomics. 12(12):3924-3934 (2013).
Spector et al.: A balanced view of the cerebrospinal fluid composition and functions: focus on adult humans. Experimental neurology. 273:57-68 (2015).
Spinal fluid proteins distinguish Lyme disease from chronic fatigue syndrome: https://www.sciencedaily.com/releases/2011/02/110223171235.htm.
Stearns et al.: Culture and molecular-based profiles show shifts in bacterial communities of the upper respiratory tract that occur with age. ISME J. 9:1246-59 (2015) https://doi.org/10.1038/ismej.2014.250.
Strehlow et al.: Osteopontin in cerebrospinal fluid as diagnostic biomarker for central nervous system lymphoma. J Neurooncol. 129(1):165-171 (2016).
Sun et al.: Lymphatic drainage system of the brain: A novel target for intervention of neurological diseases. Progress in neurobiology. 163:118-143 (2018).
Szulzewsky et al.: Loss of host-derived osteopontin creates a glioblastoma-promoting microenvironment. Neuro Oncol. 20(3):355-366 (2018).
Tanabe et al.: Cerebrospinal Fluid and Serum Neuron-Specific Enolase Levels After Febrile Seizures. Epilepsia. 42(4):504-507 (2001).

(56) References Cited

OTHER PUBLICATIONS

Vayssier-Taussat et al.: Shifting the paradigm from pathogens to pathobiome: new concepts in the light of meta-omics. Front Cell Infect Microbiol. 4:29 (2014) https://doi.org/10.3389/fcimb.2014.00029.
Whelan et al.: The loss of topography in the microbial communities of the upper respiratory tract in the elderly. Ann Am Thorac Soc. 11:513-21 (2014).
Wright et al.: Cerebrospinal fluid and lumbar puncture: a practical review. Journal of Neurology. 259(8):1530-1545 (2012).
Zheng et al.: Elevated levels of ferritin in the cerebrospinal fluid of amyotrophic lateral sclerosis patients. Acta Neurlogica Scandmavica. 136(2):145-150 (2016).
Zhu et al.: Aberrant Levels of Cystatin C in Amyotrophic Lateral Sclerosis: a Systematic Review and Meta Analysis. Int J Bio Sci. 14(9):1041-1053 (2018).
Zou et al.: SARS-CoV-2 viral load in upper respiratory specimens of infected patients. NEJM (2020) DOI: 10.1056/NEJMc2001737.
LoFric Primo product description—Wellspect: website (2020) https://www.wellspect.com/products/bladder-products/lofric/lofric-primo.
LoFric Product Catalog (2020).
Speedicath Compact Female: website (2020) https://www.coloplast.ca/speedicath-compact-female-en-ca.aspx#section=product-description_3.
Speedicath Compact Male: website (2020) https://www.coloplast.ca/speedicath-compact-male-en-ca.aspx#section=product-description_3.
Speedicath: website (2020) https://www.coloplast.ca/speedicath-1-en-ca.aspx#section=product-description_3.
Vapro Coude Touch Free Hydrophilic Intermittent Catheter: website (2020) https://www.hollister.com/en/products/continence-care-products/intermittent-catheters/hydrophilic-pre_lubricated/vapro-touch-free-hydrophilic-intermittent-catheter.
Vapro Plus Touch Free Hydrophilic Intermittent Catheter: website (2020) https://www.hollister.com/en/products/continence-care-products/intermittent-catheters/hydrophilic-pre_lubricated/vapro-plus-touch-free-hydrophilic-intermittent-catheter.
Gern et al.: Relationships among specific viral pathogens, virus-induced interleukin-8, and respiratory symptoms in infancy. Pediatric Allergy and Immunology. 13(6):386-393 (2002).
Gritzfeld et al.: Comparison between nasopharyngeal swab and nasal wash, using culture and PCR, in the detection of potential respiratory pathogens. BMC research notes. 4(1):122 (2011).
Hall et al.: Clinically useful method for the isolation of respiratory syncytial virus. Journal of Infectious Diseases. 131(1):1-5 (1975).
Hentschel et al.: Dynamics of soluble and cellular inflammatory markers in nasal lavage obtained from Cystic Fibrosis patients during intravenous antibiotic treatment. BMC pulmonary medicine. 14(1):82 (2014).
Hentschel et al.: Influences of nasal lavage collection, processing and storage methods on inflammatory markers-evaluation of a method for non-invasive sampling of epithelial lining fluid in cystic fibrosis and other respiratory diseases. Journal of immunological methods. 404:41-51 (2014).
Li et al.: Comparison among nasopharyngeal swab, nasal wash, and oropharyngeal swab for respiratory virus detection in adults with acute pharyngitis. BMC infectious diseases. 13(1):281 (2013).
Pitrez et al.: Nasal wash as an alternative to bronchoalveolar lavage in detecting early pulmonary inflammation in children with cystic fibrosis. Respirology. 10(2):177-182 (2005).
Rasmussen et al.: Resident aerobic microbiota of the adult human nasal cavity. Apmis. 108(10):663-675 (2000).
Riechelmann et al.: Biological markers in nasal secretions. European respiratory journal. 21(4):600-605 (2003).
Lumbar Puncture Complications: https://meds.queensu.ca/central/assets/modules/lumbar_puncture/complications.html (printed (Feb. 6, 2018).
MEDSCAPE: What is the role of beta-trace protein testing in the workup of cerebrospinal fluid (CSF) rhinorrhea? https://www.medscape.com/answers/861126-102445/what-is-the- role-of-beta-trace-protein-testing-in-the-workup-of-cerebrospinal-fluid-csf-rhinorrhea (Apr. 1, 2019).
Girerd et al.: In Vivo Inspection of the Olfactory Epithelium: Feasibility of Robotized Optical Biopsy. Annals of Biomedical Engineering. 46:1951-1961 (2018).
PCT/IB2020/000849 International Search Report and Written Opinion dated Jan. 27, 2021.
European Patent Application No. 19785021.7 European Search Report dated Nov. 24, 2021.
PCT/IB2020/000293 International Search Report and Written Opinion dated Oct. 29, 2020.
Chinese Application No. 2019800396809 First Office Action dated Mar. 3, 2022.

\* cited by examiner

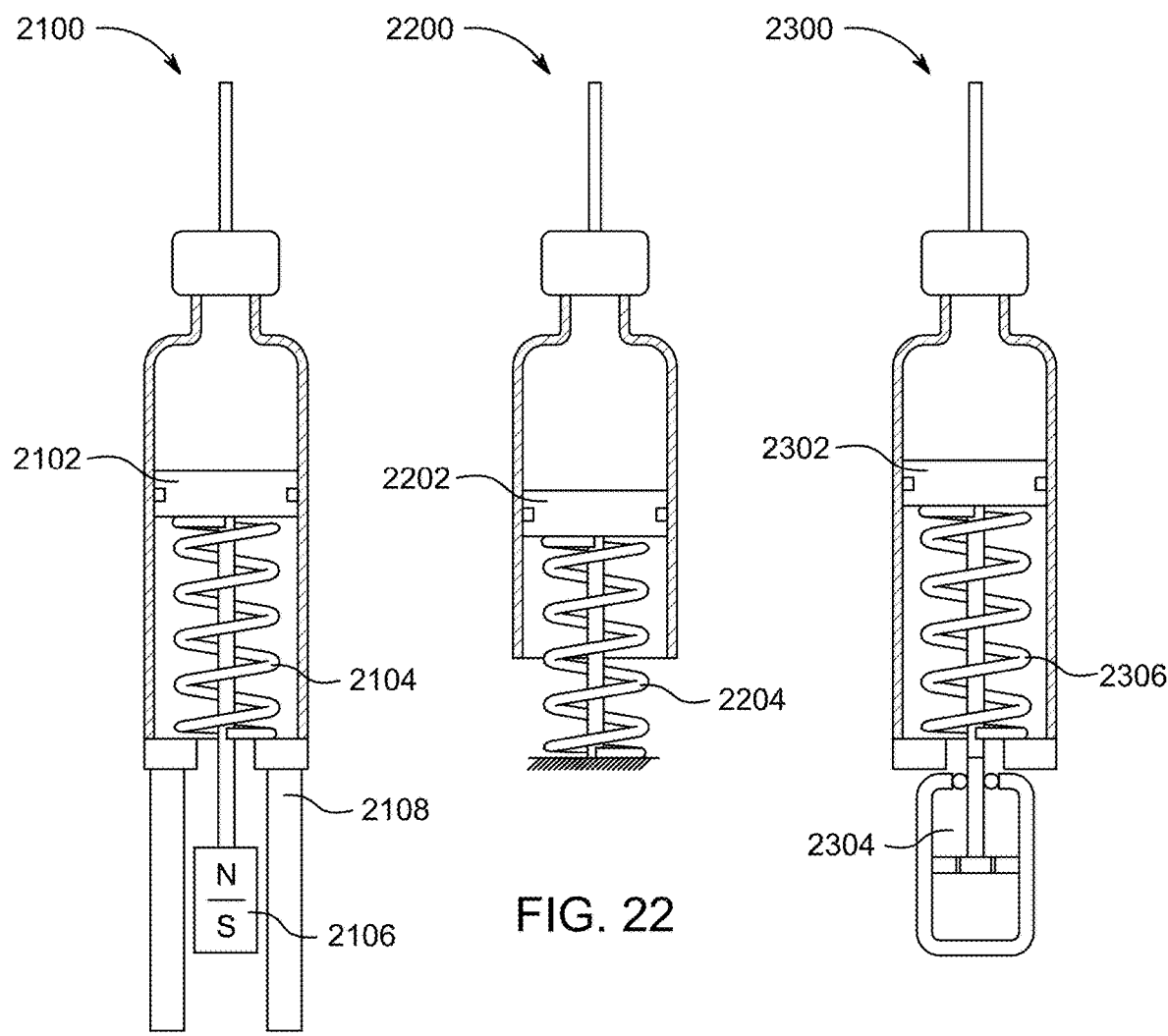

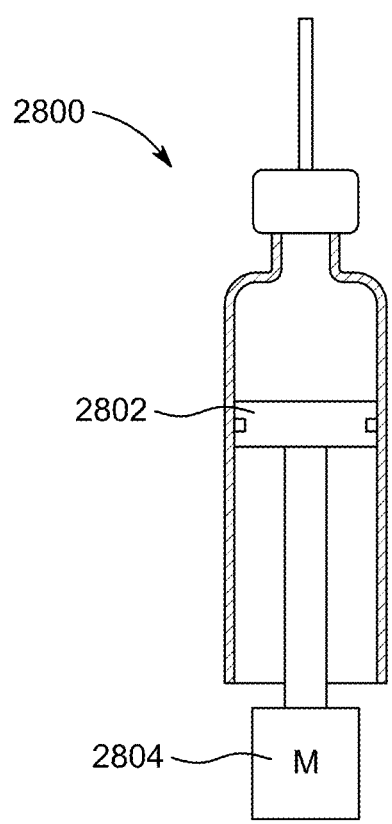
FIG. 28
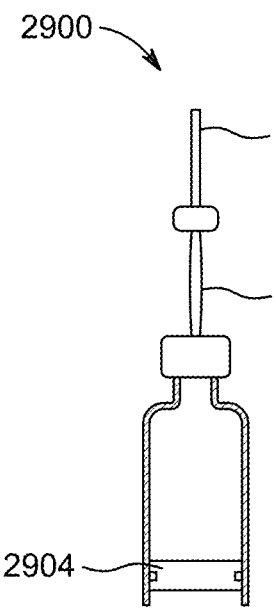 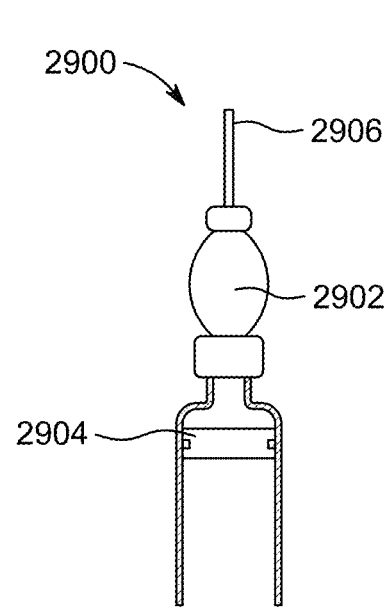 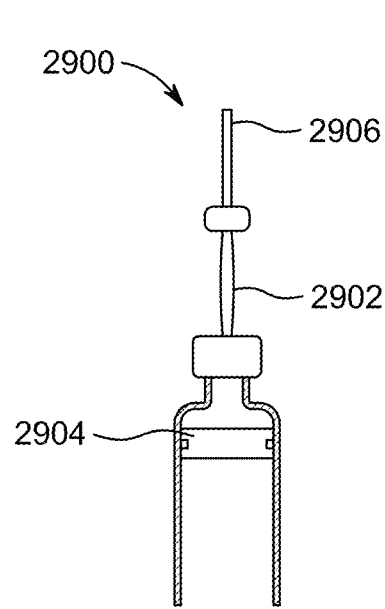
FIG. 29a          FIG. 29b          FIG. 29c

INTRANASAL DRUG DELIVERY DEVICE, SYSTEM, AND PROCESS

CROSS REFERENCE TO RELATED APPLICATIONS

This application is a continuation of International Application No. PCT/CA2019/050455, filed Apr. 12, 2019, which claims the benefit of priority of U.S. Provisional Patent Application Nos. 62/656,463 filed Apr. 12, 2018 and 62/774,444 filed Dec. 3, 2018, all of which are incorporated herein by reference in their entireties.

FIELD

The present disclosure generally relates to the field of drug delivery and intranasal devices.

BACKGROUND

There are various devices currently available for delivering drugs to the nasal cavity. Examples of prior art intranasal delivery devices include: US 2016/0367774; US 2017/0072145; US 2016/0310683; US 2013/0331916; US 2015/0165139; US 2015/0080785; US 2016/0310683; U.S. Pat. No. 7,799,337; US 2007/0789976; US 2013/0142868; US 2014/0083424; US 2011/0132354; US 2002/0017294; US 2011/0088690; U.S. Pat. Nos. 9,707,226; 8,001,963; 9,480,644; 9,550,036; 5,331,954; 6,112,743; 6,180,603; 7,296,566; 5,224,471; and 5,307,953.

The inventors have determined a need for improved intranasal delivery devices.

SUMMARY

In accordance with an aspect, there is provided an intranasal drug delivery device having compliant or flexible, soft nib to precisely locate the dosage and provide comfort for user. The term drug can also be used herein to refer to other agents such as vitamins, fragrance, saline or non-pharmaceutical agents.

In accordance with an aspect, there is provided an intranasal drug delivery device having a cocking mechanism and actuator to load and release dosage.

In accordance with an aspect, there is provided an intranasal drug delivery device having a non-air interface mechanically pressurized fluid reservoir to enable dosing independent of orientation and to load shot chamber. In some example embodiments, reservoir can be collapsible from external pressure, including ambient air pressure.

In accordance with an aspect, there is provided an intranasal drug delivery device connectable to a facial or device recognition application to prevent intentional or unintentional misuse.

In accordance with an aspect, there is provided an intranasal fluid delivery device comprising a dispensing tip connected to a hollow needle, a shot chamber carrying a fluid, the shot chamber having a diaphragm at one end and a plunger at the other end, and an actuator connected to a push rod moveable toward the shot chamber and having a locking mechanism, wherein pushing the actuator releases the locking mechanism, allowing the push rod to push against the plunger, exerting pressure on the fluid and forces the needle through the diaphragm into the shot chamber such that the fluid flows out of the needle into the dispensing tip.

In accordance with an aspect, there is provided apparatus for delivering fluid to a nasal volume comprising a housing having a first end with a dispensing opening and a second end with an actuating opening, a dispensing tip coupled to the dispensing opening, a capsule within the housing between the actuating opening and the dispensing opening, the capsule comprising a tube pre-filled with fluid between a diaphragm and a plunger, and, an actuator coupled to the actuating opening, the actuator comprising a push rod moveable into contact with the plunger and held back by a locking mechanism, and a spring urging the push rod toward the plunger.

In accordance with an aspect, there is provided a method for targeted intranasal fluid delivery. The method comprises inserting a compliant dispensing tip into a nasal cavity, and ejecting a fluid from the compliant dispensing tip to deliver a laminar liquid bolus to a targeted region within the nasal cavity. The targeted region may be an olfactory region of the nasal cavity. Inserting the compliant dispensing tip into the nasal cavity may comprises inserting the compliant dispensing tip at least into an upper nares. Inserting the compliant dispensing tip into the nasal cavity may comprise positioning an end of the compliant dispensing tip proximate to the olfactory region. The compliant dispensing tip may comprise a cannula. Ejecting the fluid may comprise ejecting the fluid with a controlled velocity profile to limit shear forces on the fluid.

In various further aspects, the disclosure provides corresponding systems and devices, and logic structures such as machine-executable coded instruction sets for implementing such systems, devices, and methods.

In this respect, before explaining at least one embodiment in detail, it is to be understood that the embodiments are not limited in application to the details of construction and to the arrangements of the components set forth in the following description or illustrated in the drawings. Also, it is to be understood that the phraseology and terminology employed herein are for the purpose of description and should not be regarded as limiting.

Many further features and combinations thereof concerning embodiments described herein will appear to those skilled in the art following a reading of the instant disclosure.

DESCRIPTION OF THE FIGURES

Description

FIG. 21 shows an example intranasal drug delivery device according to some embodiments.

FIG. 22 shows an example intranasal drug delivery device according to some embodiments.

FIG. 23 shows an example intranasal drug delivery device according to some embodiments.

FIG. 28 shows an example intranasal drug delivery device according to some embodiments.

FIGS. 29 a-c show an example intranasal drug delivery device according to some embodiments.

DETAILED DESCRIPTION

Embodiments of methods, systems, and apparatus are described through reference to the drawings.

Currently disposable intranasal drug delivery devices are characterized by low accuracy/uniformity of drug dosing, no design for anatomic variability and poor design for human factors—efficacy and safety. The applications where these shortcomings are most detrimental are: direct-to-brain delivery path (uptake through olfactory epithelium into CSF, action in brain), systemically acting drugs (uptake through mucosa into vasculature, systemic action), vaccines (uptake and action in mucosa), and topically acting drugs (uptake and action in mucosa).

The following provides for intranasal delivery of new and existing drugs, with the following benefits: less cost, increased effectiveness, increased safety (both to patient and society), and increased convenience (in terms of health care).

The following provides for opportunities in terms of design for markets where access to health care is challenged (humanitarian impact) and in terms of design for prevention of drug misuse.

Figure 1:
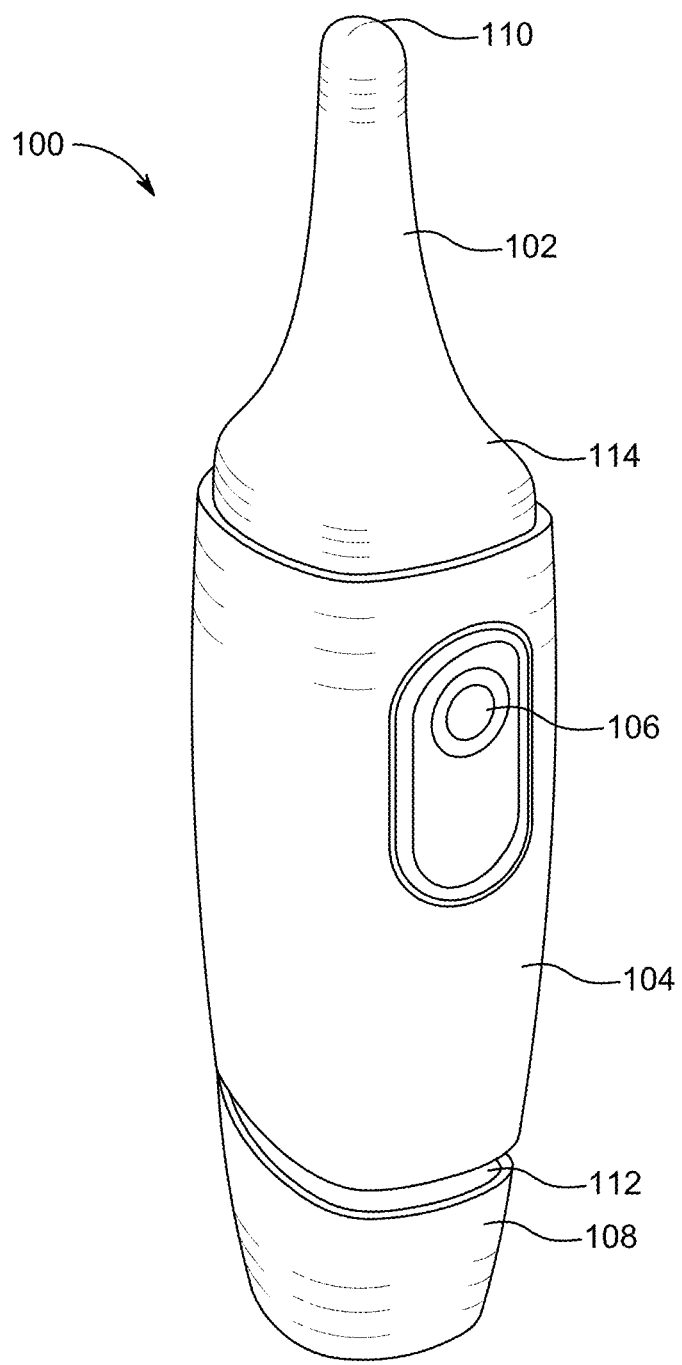
FIG. 1 shows an example intranasal drug delivery device according to some embodiments.

FIG. 1 shows an example intranasal drug delivery device 100 according to some embodiments.

The device 100 has a compliant or flexible, soft nib 102 (as opposed to a hard nib) to precisely locate the dosage. The soft nib 102 also provides comfort for user and may minimize blocking by the nasal wall or congestion.

Septal deviation can cause different health related problems. In some embodiments compliant, soft nib 102 conforms to the anterior aspect of the intranasal passage. In some embodiments the soft nib 102 is biased to follow the patient's septum. This allows the tip 110 to be placed in a location in the nasal cavity to discharge medicine targeting the olfactory region and accommodates differences in nasal cavity anatomy.

Figure 34:
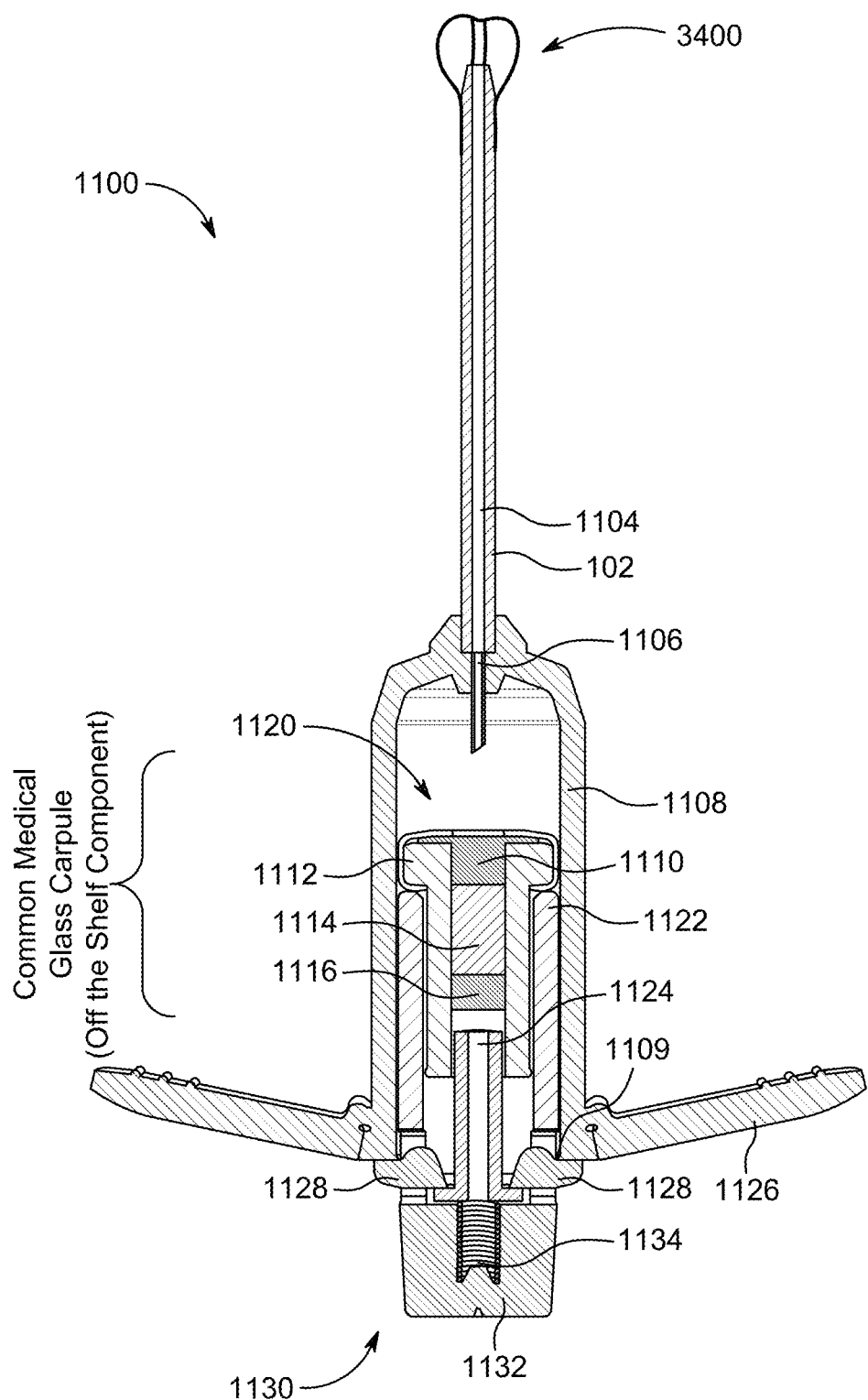
FIG. 34 shows an example intranasal drug delivery device with a dispensing tip having a bulbous end portion according to some embodiments.
Figure 35:
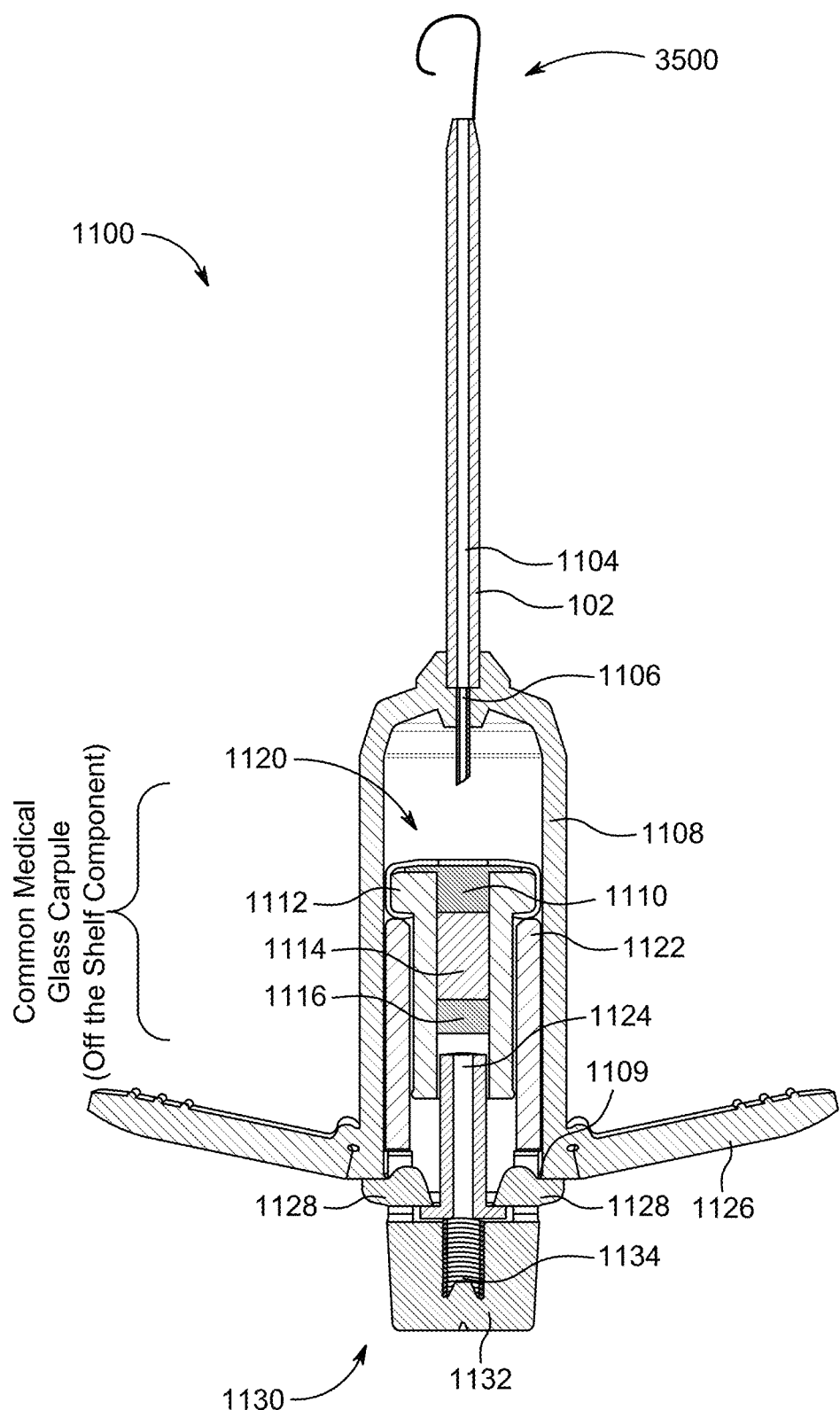
FIG. 35 shows an example intranasal drug delivery device with a dispensing tip having an alpha loop according to some embodiments.

In some embodiments compliant, soft nib 102 has a kiss-cut valve near the tip 110. The valve reduces the partial discharge at the front and backend of the actuation. The tip 110 also reduces or eliminates air or contaminates from contacting the line-fill remaining in the nozzle between dosing. In some embodiments the orientation of the kiss cut is off set from the end of the tip 110 for directing the medicine in the direction of the olfactory region of the nasal anatomy. The nib 102 can be a multiple material overmoulded nib in some embodiments. As shown in FIG. 34, in some embodiments the nib may have a bulbous or ball shaped end portion 3400 to ease the insertion and facilitate better laminar flow along the nasal ridge. As shown in FIG. 35, in some embodiments, the compliant nib utilizes an 'alpha loop' 3500 to facilitate positioning an end of the dispensing tip past an obstruction. One of the tricks in interventional cardiology to pass a guidewire past a stricture or calcified obstruction is to force the flexible tip guide wire into the obstruction. The tip will naturally bend back on itself and the wire finds its way through the obstruction with the alpha loop leading. The larger bearing surface helps to steer the wire to the point of least resistance and it will slip through the stricture/obstruction. This embodiment may be utilized in trauma where a nose may be less than perfect, this could be the shape that would help the compliant nib find its mark.

The device 100 has an actuator 106 (e.g. button, trigger) and cocking mechanism 108 to release dosage that is reproducible to reduce human error/variation. Use of a cock-and-release mechanism in some embodiments promotes steady positioning during delivery and reduces the need for priming of the device 100, thereby reducing the possibility of operator error. In some embodiments a finger press button actuation discharges the shot chamber. This method of actuating the device 100 requires very little dexterity or fine motor skills which may be of particular importance to patients whose motor skills may be impaired e.g. patients with Parkinson's. Priming can refer to ensuring full liquid filling dosing/metering mechanism suitable for pumping of the liquid including but not limited to positive displacement pumping.

The device 100 has an internal reservoir that can be under pressure constantly in some embodiments to enable dosing independent of orientation (e.g. the user can be standing up or laying down and it will work). The reservoir may be a bag and may be collapsible by external pressure, including ambient air pressure. The pressure within the reservoir may change depending on the spring used, but it can always be under some amount of pressure.

In some embodiments the device 100 has no air-port for filling, storing or actuating the device 100. This allows for traveling or transport by air, particularly unpressurized aircraft or higher elevations and may be useful for oxygen sensitive medicine and extending shelf life of certain medicines, particularly where there is no cold-chain infrastructure. In addition, this makes the device difficult to tamper with. In some embodiments, there can be an air bleed port.

In some embodiments the shape of the device 100 allows for correct nozzle positioning and ergonomic grip that does not engage the shoulder, wrist, or any part of the other arm not activating the device 100. The design of device 100 promotes minimal use of shoulder and arm movement.

In some embodiments the design of device 100 is made highly ergonomic in form, taking inspiration both from a wider remote controller design and a more dexterous pen design.

The ergonomics and considered human factors create a step change in the state of the art for nasal delivery devices. The design minimizes human error, allowing for a targeted, repeatable, and metered dose delivery. The design accommodates a consumable drug reservoir for short to long term use, while allowing for a low cost single patient consumable. This gives the ability for a wide variety of drugs to be filled at the point of care or by pharmaceutical filling lines. The design allows for, as an example, a compliant, soft nib 102 with an ultra-soft, matte finish, elastomeric shroud.

The compliant, soft nib 102 of the device is entered into the intranasal cavity and uses the common internal nasal geometry to guide the tip proximate to the olfactory region. The compliant soft nib 102 stops at a distance from the olfactory region and the ejected drug bolus is guided to the olfactory by the native geometry of the nasal anatomy. The device mechanism supports a pocketable form being based on compact and low-cost injection-mouldable parts.

Figure 2:
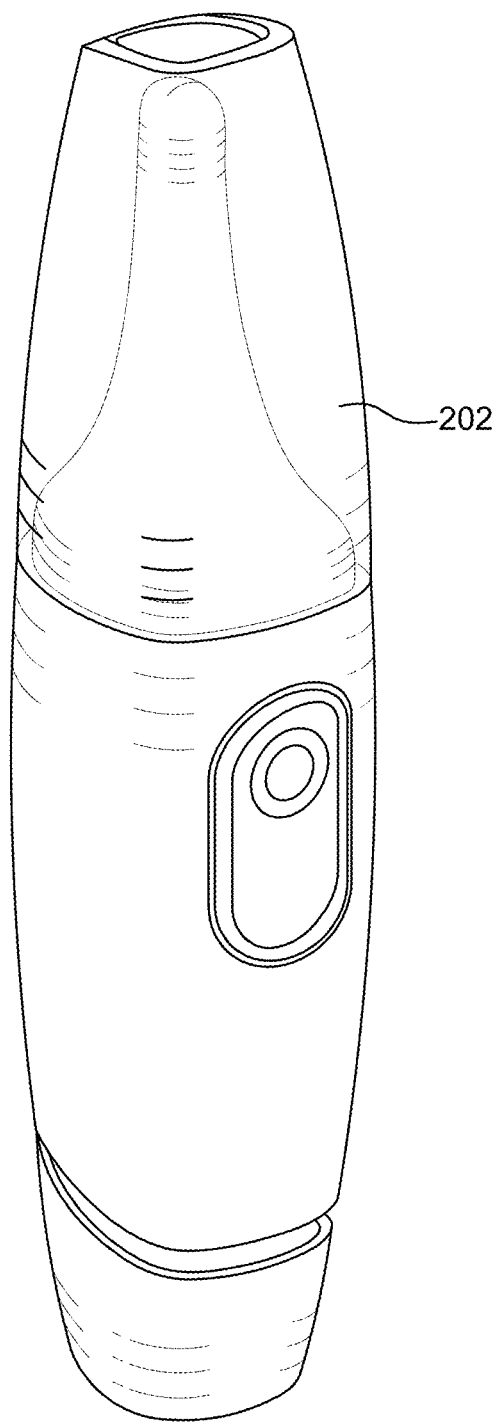
FIG. 2 shows an example intranasal drug delivery device with a lid or cap according to some embodiments.

FIG. 2 shows an example intranasal drug delivery device 100 with a lid 202 or cap according to some embodiments.

In some embodiments the lid 202 may be used with the cocking mechanism 108, or instead of cocking mechanism 108, as part of reloading the intranasal drug delivery device 100. The addition of the lid 202 increases the grip size of the drug delivery device 100 and prevents misfiring of the drug delivery device 100. In some embodiments lid 202 may provide extra space for full hand grip when attached to bottom of device 100. In some embodiments lid 202 is shaped to increase the surface area without obstruction by hand when in use so that machine readable indicia (i.e. URL code) can be added to the increased surface area.

In some embodiments, the device 100 may include rechargeable energy storage to provide motive energy with separate actuation. Rechargeable energy may include electrical, chemical or pressurized fluid storage.

Figure 3:
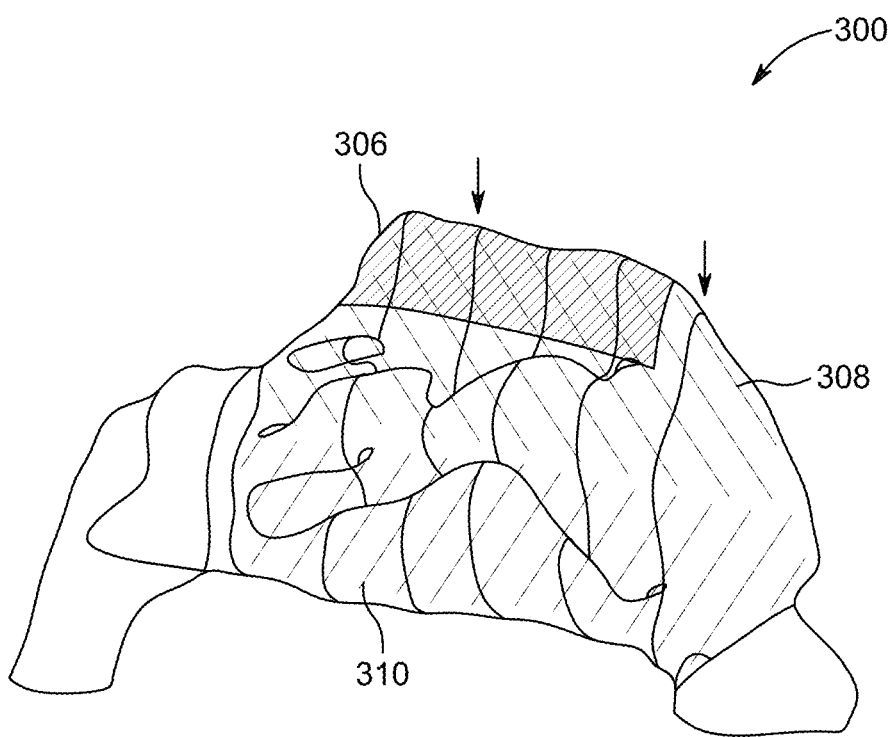
FIG. 3 shows an illustration of the olfactory region.

FIG. 3 shows an illustration of the nasal cavity 300 including the olfactory region 306, upper nares 308 and lower nares 310.

In topical drug delivery, drug is delivered to the entire mucosa, i.e. both the upper nares 308 and lower nares 310. In systematic drug delivery, drug is delivered through the mucosa of the upper nares 308 into the vasculature. In direct-to-brain drug delivery, drug is delivered mainly through the olfactory region 306 diffusion through the olfactory mucosa. The olfactory path may be short and drugs might be transported through the cribriform plate within the cerebrospinal fluid draining from olfactory bulb. This may also involve the participation of trigeminal nerves.

Current drug formulations for nasal delivery use standard sprays with no specificity to the olfactory region 306, relatively small molecules are used, and formulations are mainly water-based with some alcohols. For non-active ingredients in drug formulations for nasal delivery a wide variety of functionality is used: solvents, mucoadhesive, agents, absorption enhancers, viscosity modifiers, pH buffers, antioxidants, preservatives, surfactants and more.

The majority of airflow passes through the lower nares 310. Therefore, sneezing would likely not expel liquids deposited in the olfactory region 306. Nasal congestion may affect mainly the lower nares 310 while the olfactory region 306 stays clear.

Targeted direct-to-brain drug delivery may be achieved through saturation of the olfactory region 306 with an excipient/drug combination. The drug may travel via extracellular transport to the Central Nervous System, via the cribriform plate. This targeted delivery is intended to reduce both topical and system delivery, allowing for safer and more effective drug delivery.

In some embodiments the device 100 may be adapted by the addition of a lateral atomizer tip to achieve the current state of the art of topical drug delivery by saturating the entire mucosa, or systemic drug delivery by targeting the Upper Nares 308.

The Olfactory plateau is generally located to the posterior aspect of the Radix line. This correlates to the Nasal Bridge length, which is measured from the soft tissue of the Nasion (Sellion) to the Subnasale.

Figure 4:
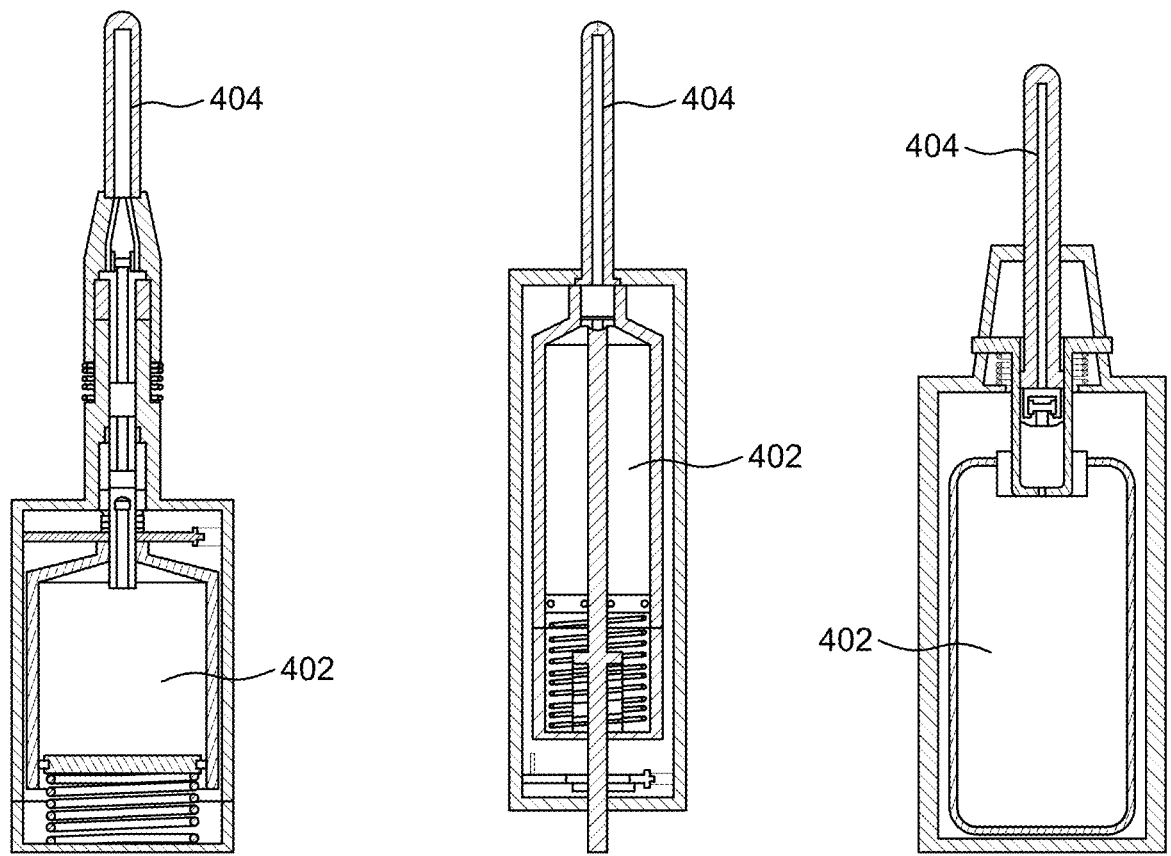
FIG. 4 shows examples of intranasal drug delivery devices according to some embodiments.

FIG. 4 shows examples of intranasal drug delivery devices according to some embodiments with reservoir 402 and compliant tip 404.

Figure 5:
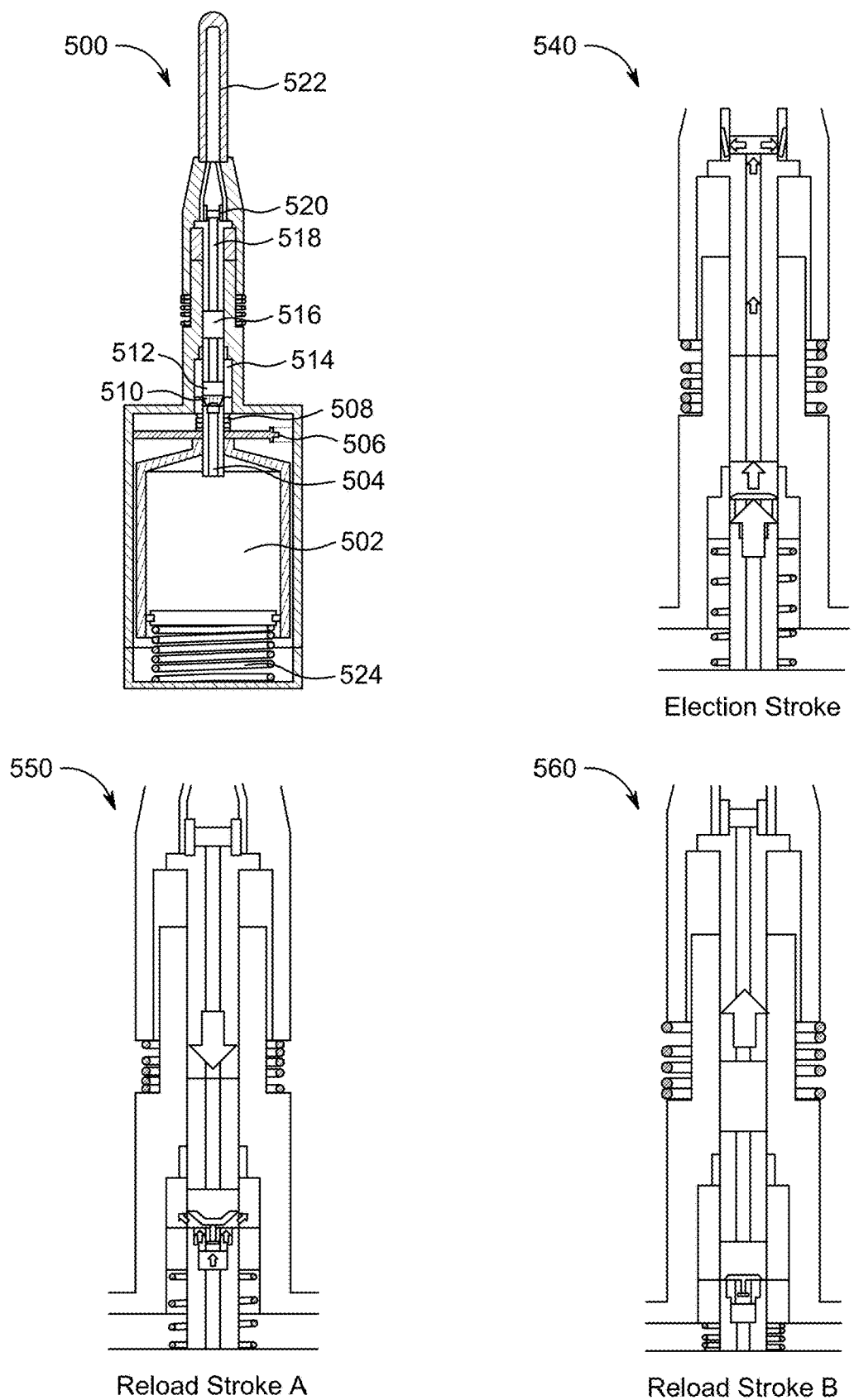
FIG. 5 shows an example ejection stroke and reload strokes of an intranasal drug delivery device according to some embodiments.

FIG. 5 shows an example release and reload mechanism 500 according to some embodiments. Release and reload mechanism 500 may be incorporated into an intranasal drug delivery devices such as, for example, device 100.

The release and reload mechanism 500 has a reservoir 502 containing a drug for delivery into the nasal cavity.

The release and reload mechanism 500 has an insertion needle 504 for insertion into the reservoir 502.

In some embodiments reservoir 502 is a bag and may be collapsible by external pressure, including ambient air pressure.

In some embodiments, reservoir 502 is removable and insertion needle 504 is inserted through a silicon stopper in the top of reservoir 502 for drawing the substance into the device 100. The silicon stopper has re-sealing properties for air sensitive medicine. The insertion needle 504 can be left in the bottle from which the medicine for the device was obtained. The filling process can eliminate the need for a separate syringe. In some embodiments, this may be referred to as a lure lock.

The release and reload mechanism 500 has actuator 506 connected to release spring 508.

The release and reload mechanism 500 has plunger 510, load valves 512 and load chambers 514.

The release and reload mechanism 500 has shot chamber 516, fluid chamber 518, release valves 520 and nozzle 522. The nozzle 522 may be in fluid communication with the nib 102 such that fluid is ejected from nozzle 522 and through nib 102 or as described below.

In some embodiments release valves 520 may comprise an elongated duckbill valve in tip to reduce and valve the line/dead volume.

In some embodiments, reservoir 502 is held under tension by compression spring 524. A constant and predetermined fluid pressure may be maintained by compression spring 524 pushing up from the bottom of the reservoir towards the shot chamber 516 and nozzle 522 and plunger 510. This constant liquid pressure charges the load chamber 514 without exposing the medicine to air or metal springs typical in most nasal pumps. In some embodiments, this may avoid the use of tubing between the reservoir 502 and shot chamber 516. This can reduce dead volume of medication or medication left in line after use. This can ensures dosing accuracy is not compromised by air entering the shot chamber 516 and no content remains in the shot chamber 516 or reservoir 502 after the last usable medicine was administered. The constant pressure enables dosing independent of user orientation.

In some embodiments the compliant, soft nib 102 is designed to discharge a laminar flow and this may include a turbulent boundary, discreet liquid slug ideally suited for maximizing dose delivery to the flat narrow section of nasal cavity leading up to the olfactory region. Delivery of laminar liquid slug assists in capillary action required for maximum medicine reaching the olfactory. In some embodiments, the laminar stream is created by tube array or hydrodynamic focusing.

In some embodiments the design of the chamber and fluid path can promote high accuracy in ejected volume.

In some embodiments device 100 is cocked by pushing down, or compressing, the bottle. This method of preparing the device for actuating requires very little dexterity or fine motor skills. This method of preparing the device for administrating medicine may be of particular importance to patients whose motor skills may be impaired e.g. patients with Parkinson's. The device can be oriented in any direction and the reloading of the shot chamber and the shot performance will not be affected i.e. the device is not gravity sensitive.

In some embodiments the compliant, soft nib 102 is extended by cocking the device. This reduces over length profile of the device for shipping, shelf space and pocketing. In the resting position the device has a less 'menacing' look.

In some embodiments cocking the device 100 may activate a dose counter. In some embodiments cocking may activate a separate shot counter for each dosing session.

In some embodiments cocking may activate a dose delay. In some embodiments cocking may activate a timer to remind patient when to activate between shots needed for dosing session. The delay between shots accommodates drug dosing indications including the timing of maximum drug absorption via the olfactory tight junction and the natural clearing of the mucosa cilia.

In some embodiments cocking may change the exposed color 112 between the upper bottle sleeve 104 and base 108. This, along with an extended nozzle tip (which in some embodiments does not fit in the lid 202 while cocked) gives the patient or care giver a clear visual and/or feel the device is ready for dosing or storage. In some embodiments exposed color 112 is made with glow plastic for darkness which promotes ease and convenience of nighttime use and for patients sensitive to light e.g. for administering medicine that dilates pupils.

In some embodiments nozzle has an adjustable nostril stop 114. This stop gives patient feedback the nozzle has arrived at the optimum nostril depth. The stop also reduces sniffing/snorting during activation.

In some embodiments, the drug may be delivered by the intranasal drug delivery device 100 by delivery of a liquid jet, burst or plug, rather than a spray. In some embodiments the design of the compliant, soft nib 102, the nozzle 522, and the valves in the reload mechanism 500 may be designed to optimize laminar ejection of drug.

Technology for liquid delivery works for a wide variety of liquid properties. This technology may be adapted to olfactory, systemic and topical delivery of drugs through an intranasal drug delivery device 100.

In some embodiments intranasal drug delivery device 100 may use particular liquid properties (such as viscosity and surface tension) to ensure prolonged residence of the delivered liquid in the target area (i.e. the olfactory region) due to capillary bridging.

In some embodiments intranasal drug delivery device 100 may include excipients in the liquid drug for delivery with particular characteristics. For example, excipients may have thixotropicity (higher viscosity at rest which improves residence time in the olfactory region 306, and lower viscosity at under shear which improves ease of metering and delivery) through additives such as cellulose. As a further example, excipients used may impact surface tension of a drug to promote wetting and capillary bridging in olfactory region. As a further example, excipients used may be pre-approved by the Federal Drug Administration for shorter development time.

In some embodiments intranasal drug delivery device 100 may include a measurement method or accessory to determine the ideal compliant, soft nib 102 size, or nozzle 522 type.

In some embodiments intranasal drug delivery device 100 may include a mechanical or electronic timer and/or lock mechanism to prevent overdosing. Intranasal drug delivery device 100 may incorporate use of mobile technology for identifying users and tracking use to prevent overdosing. Intranasal drug delivery device 100 may incorporate use of a cock-and-release mechanism to promote steady positioning during drug delivery. These additions assist with patient compliance.

In some embodiments intranasal drug delivery device 100 may be used in one or more of the following applications: 1) drugs directly targeting the brain via the olfactory region, 2) systemically acting drugs (e.g. better systemic bioavailability or less degradation than via the GI tract), 3) vaccines eliciting a mucosal immune response, and 4) topically-acting drugs.

In some embodiments the intranasal drug delivery device 100 may have one or more of the following features: 1) hand held, 2) useable with a single hand, 3) designed for ambidextrous use, 4) the priming mechanism is simple and intuitive to the user, 5) there is a clear indication when the dose is primed, 6) the form promotes proper positioning in the nasal cavity, 7) designed to require a single user action to deliver a primed dose, 8) designed to prevent the user from dispensing partial doses, and 9) useable for multiple doses.

In some embodiments the intranasal drug delivery device 100 is intended to be filled by a pharmacist or other medical professional. In some embodiments the intranasal drug delivery device 100 shall contain means for preventing unintended refills of the reservoir 502.

In some embodiments the intranasal drug delivery device 100 is designed for multiple uses. In some embodiments the intranasal drug delivery device 100 uses a disposable or a refillable reservoir 502. In some embodiments the compliant, soft nib 102 is disposable.

In some embodiments intranasal drug delivery device 100 is designed with a floating gasket in a disposable or reusable reservoir 502.

In some embodiments, the drug delivery device 100 may integrate with a system involving mobile technology such as, for example, face recognition and position tracking, Gyroscopic position tracking of device and correlation with facial position, use of NFC to track number of shots.

In some embodiments, the drug delivery device 100 may enable electrically activated drug delivery such as Iontophoresis. In some embodiments, the drug delivery device 100 may involve applying an ionic charge to the drug molecule to enhance transport. In some embodiments, the drug delivery device 100 may involve an extending tip that telescopes.

In some embodiments, intranasal drug delivery device 100 is designed to use a foam as an excipient to assure residence time in target area yet allow air to pass.

In some embodiments intranasal drug delivery device 100 has barbs to lock a gasket at the end of travel to prevent misuse by refilling.

In some embodiments intranasal drug delivery device 100 has a piston that scores the chamber walls as it travels to the top of the reservoir with each actuation. This renders the device useless after a single use.

In some embodiments intranasal drug delivery device 100 is a multi-dose device with a sterile barrier to avoid contamination.

Figure 6:
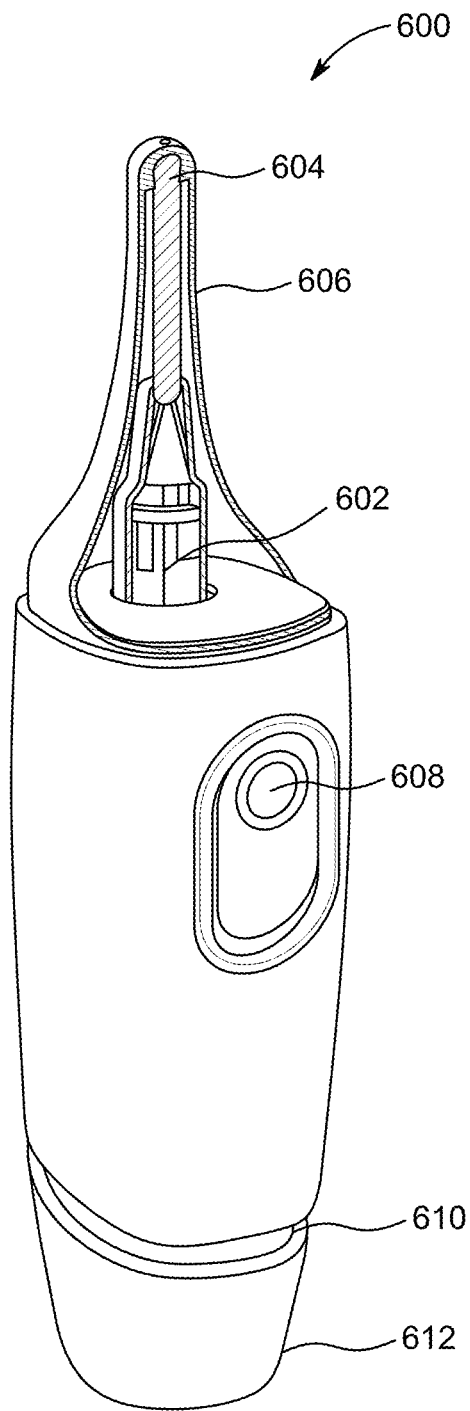
FIG. 6 shows an example internal view of a tip and tip mechanism of an intranasal drug delivery device according to some embodiments.

FIG. 6 shows an example intranasal drug delivery device 100 according to some embodiments including fluid chamber 602, nozzle 604, compliant, soft nib 606, actuator 608, exposed colour 610 and base 612.

Figure 7:
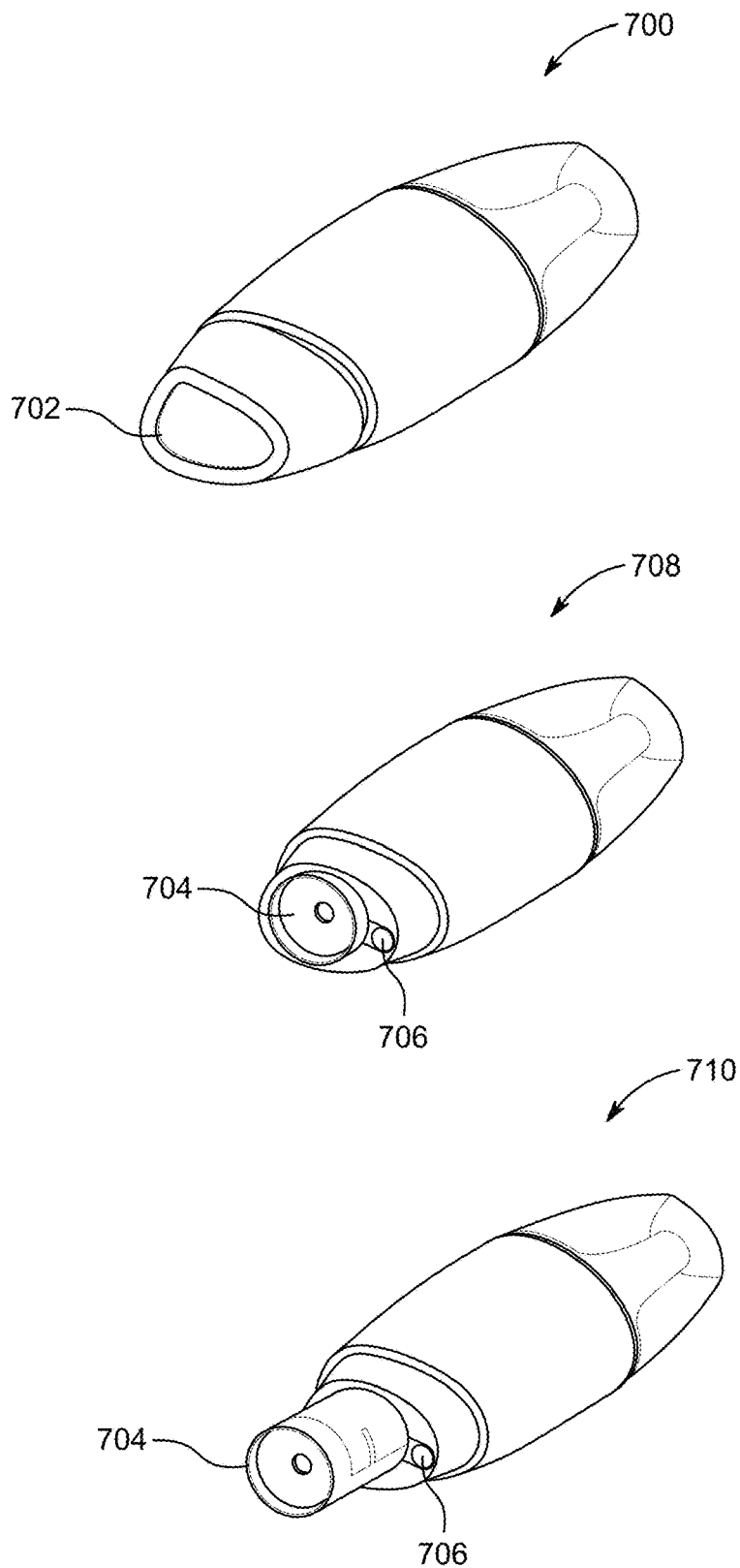
FIG. 7 shows an example intranasal drug delivery device with a removable reservoir according to some embodiments.

FIG. 7 shows an example intranasal drug delivery device 700 708, 710 according to some embodiments: with the base 702 connected to the intranasal drug device 700, with the base 702 removed and the removable reservoir 704 inserted into the intranasal drug delivery device 708, and with the removable reservoir 704 partially removed from intranasal drug delivery device 710. In some embodiments, a latch mechanism 706 retains the removable reservoir 704 in the device.

Figure 8:
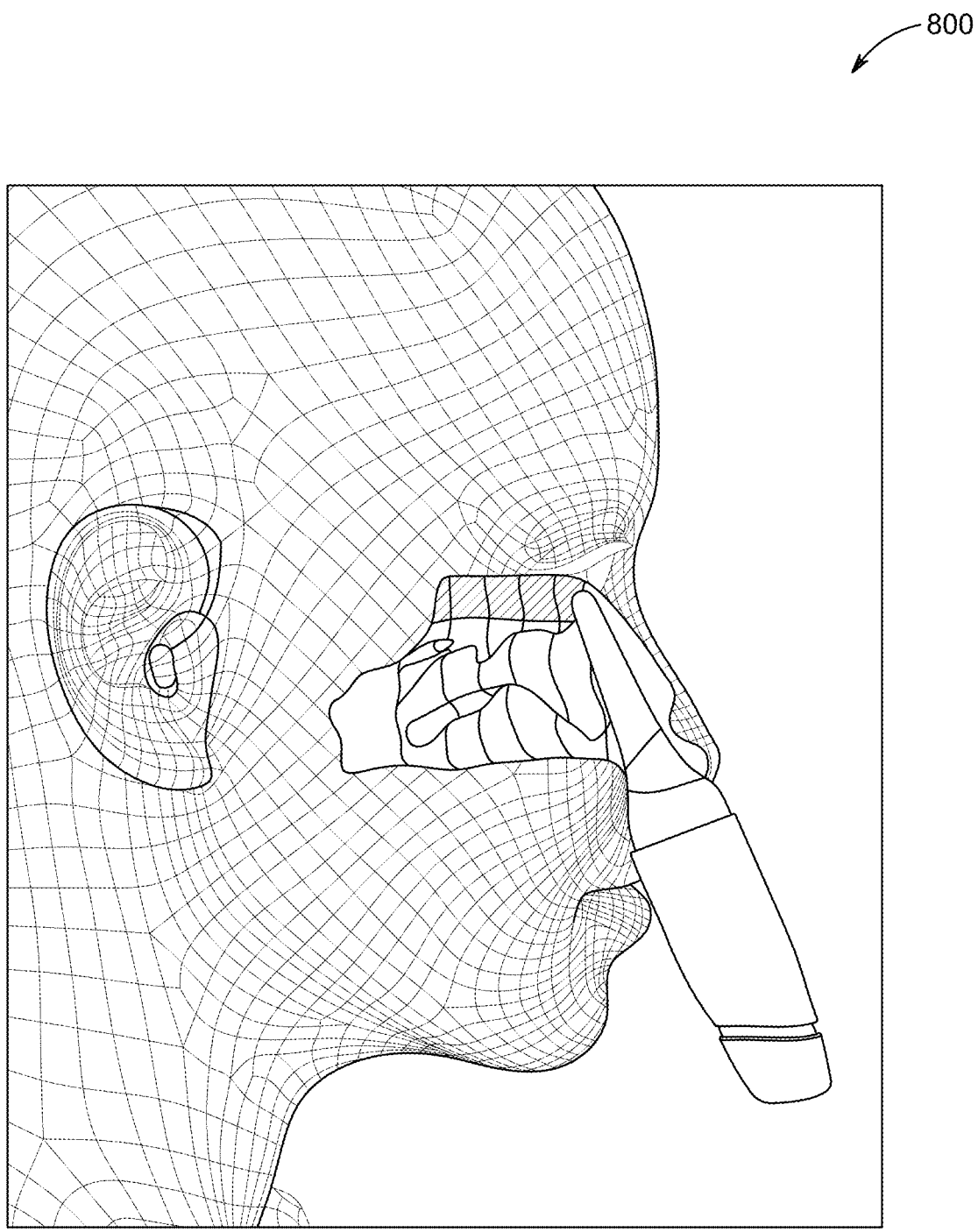
FIG. 8 shows an example intranasal drug delivery device according to some embodiments with the tip inserted in the nasal cavity.

FIG. 8 shows an intranasal drug delivery device 100 inserted into the nasal cavity of a patient with the tip touching the olfactory region 306. In some embodiments a speculum may be used as an accessory to open the nostril. In some embodiments the device 100 may be include an accessory part to guide the tip.

The compliant, soft nib 102 of the device is entered into the intranasal cavity and uses the common internal nasal geometry to self-guide the compliant, soft nib 102 to the olfactory region. The compliant, soft nib 102 is held from lateral deviation via the flanking medial septum, and the lateral nasal wall.

In some embodiments when the device 100 is activated, an internal metering chamber ejects a repeatable and metered dose into the superior/posterior aspect of the olfactory region. A laminar flow is produced, as opposed to conventional atomization or spray, to ensure that the ejected dose gets delivered to the target area, rather than spreading in the entire intranasal space. Due to the Coanda effect, the ejected excipient adheres to the medial, lateral and superior aspect of the olfactory corridor while still motive.

When the motive energy of the ejected liquid has dissipated, opposing wall capillary motion allows the excipient to coat the entire olfactory area. This is due to the combination of excipient surface tension (which is caused by cohesion within the excipient) and mucoadhesive properties between the excipient and olfactory mucosa wall.

To achieve residence time, and as a result of capillary action, the excipient will be held in the olfactory corridor due to a capillary bridge effect caused by the opposing walls of the medial, lateral and superior aspect of the olfactory corridor. Thus preventing the excipient from draining to the inferior aspect of the nasal vault. An adequately high viscosity or thixotropic property of the excipient helps prolonging residence time.

In one embodiment the proposed method for targeted drug delivery using the device 100 is as follows: 1) The compliant tip is placed to the anterior aspect of the olfactory corridor; 2) The excipient is ejected out of the tip in a "reasonably" laminar jet, and towards the posterior aspect of the olfactory corridor; 3) Due to the Coanda effect, jet ejection will cause the excipient to adhere to the medial, lateral and superior aspect of the olfactory corridor while still motive; 4) When the motive energy of the ejected liquid has dissipated, opposing wall capillary motion allows the excipient to coat the entire olfactory area. This is due to the combination of excipient surface tension (which is caused by cohesion within the excipient) and mucoadhesive properties between the excipient and olfactory mucosa wall; 5) To achieve residence time, and as a result of capillary action, the excipient will be held in the olfactory corridor due to a capillary bridge effect caused by the opposing walls of the medial, lateral and superior aspect of the olfactory corridor. Thus preventing the excipient from draining to the inferior aspect of the nasal vault. An adequately high viscosity or thixotropic property of the excipient helps prolonging residence time.

Figure 9:
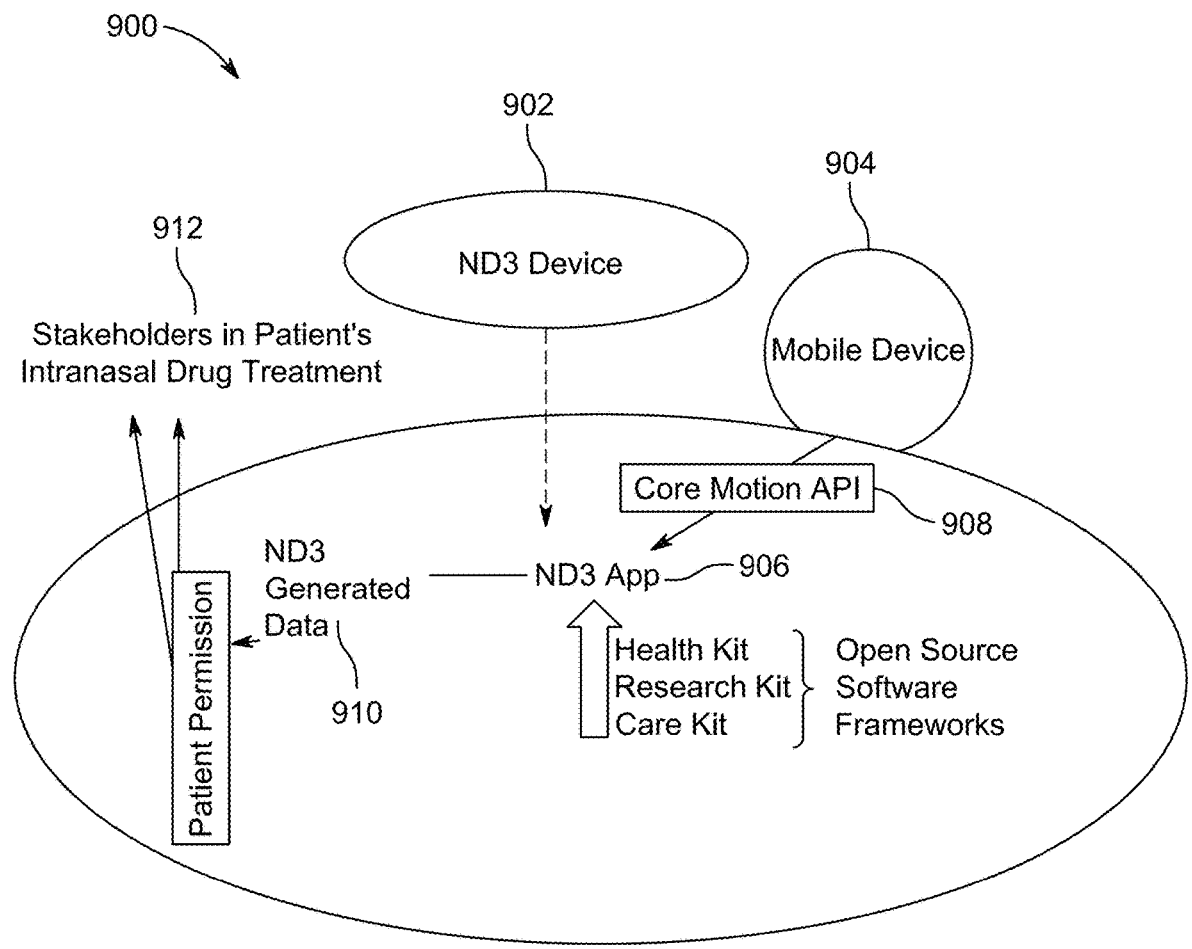
FIG. 9 shows an illustration of an integrated intranasal drug-delivery platform.

FIG. 9 illustrates an integrated intranasal drug-delivery platform 900 including an intranasal drug delivery device 902, a mobile device 904, an intranasal device software application 906, a core application program interface 908, and device generated data 910 that may be shared with shareholders 912.

The device 902 can connect to a software application 906 installed on a mobile device 904 for data logging to flag or track misuse and compliance. For example, the intranasal device software application 906 can capture images up the nasal cavity to flag misuse, implement user biometric authentication for compliance, capture timing data of dosage for compliance, provide alerts or reminders to user and so on.

In some embodiments a software application will be available in association with the device 100 to create an integrated hardware and software intranasal drug-delivery platform 900. This includes a database for the storage of data generated from device 100 that serves as a basis for extension to a permission-based personal data ecosystem platform.

In some embodiments the software application may be extended to become a platform for more broad data aggregation and permission-based sharing. A patient's personal data could be collected and exchanged with permission to/from all parties who have a role and accountability for administering (dispensed and applied) intranasal treatments. The data exchange portal would provide patient insight aimed at aligning and continuously influencing positive behavior for optimum health care delivery. The extension will facilitate sharing of different types of smartphone-based personal data to different stakeholders such as other patients, guardians, doctors, clinics, clinical trial researches, health care providers, patient medical insurers, doctor insurers, health care insurers, drug developers, pharmacies, patient peer support groups, disease/disorder researchers, disease/disorder NGO's, government regulators, law enforcement/first responders. Privacy and control of personal data are important. A user may wish to share data in certain circumstances, based on incentives or goodwill.

In some embodiments components of an integrated intranasal drug-delivery platform 900 may comprise an intranasal drug delivery device 902 that is inextricably linked with a specified medicine and an individual patient through device and patient verification; intranasal drug delivery device 902 that provides machine readable signals (fiducial markers) at time of scrip writing, scrip filling, patient dosing, patient possession, and device redemption (i.e. patient life cycle events); ongoing data harvesting, transit, storage and retrieval capability; aggregation and anonymization of personal data into mineable and usable data sets eg. reporting, analytics, gamification, incentivizing, etc.; personal data for optimizing patient's immediate and ongoing healthcare and a permission-based sharing system.

Categories of data that an integrated intranasal drug-delivery platform 900 may utilize include a patient profile; stakeholder profiles to manage data that has been shared with them; non-medical passive personal data (recovery of which may be ongoing); medical/biometric personal data (recovery of which may be ongoing); event driven personal data at time of scrip writing, scrip filling, patient dosing, patient possession, and device redemption (i.e. patient lifecycle); and event driven prompting to influence immediate behavior.

For an example of an integrated intranasal drug-delivery platform 900 for a user that has been prescribed a drug that is dispensed with intranasal drug delivery device 902, 1) the user receives an alert on his/her mobile device 904 signaling that it's time to take a scheduled dose of drug, 2) the user unlocks the mobile device 904 using native identity authentication (passcode, fingerprint or facial recognition) and the intranasal device software application 906 opens on the mobile device, 3) the user touches the mobile device 904 to the intranasal drug delivery device 902 or initiates another form of recognition, 4) the user uses the mobile device 902 for facial recognition validation, 5) the intranasal device software application 906 prompts the user for measuring pre-actuation metrics/biometrics (relevant metrics may be determined by clinician, for example, cognition survey, HR measurement, short video capture to determine emotional state/impairment etc.), 6) the user completes any inputs needed to complete pre-actuation tests, 7) the intranasal device software application 906 determines that the intranasal drug delivery device 902 has been actuated (the action may be timestamped and recorded, methods for confirming actuation include Bluetooth connectivity, visual image, sound, colour change, artificial intelligence that recognizes actuation), 8) the intranasal device software application 906 prompts the user for measurements of post-actuation biometrics (relevant metrics may be determined by clinicians); 9) the user is taken back to dashboard as part of an interface controlled by software application 906 where he/she can track different metrics and manage permissions (who can see what data).

Figure 10:
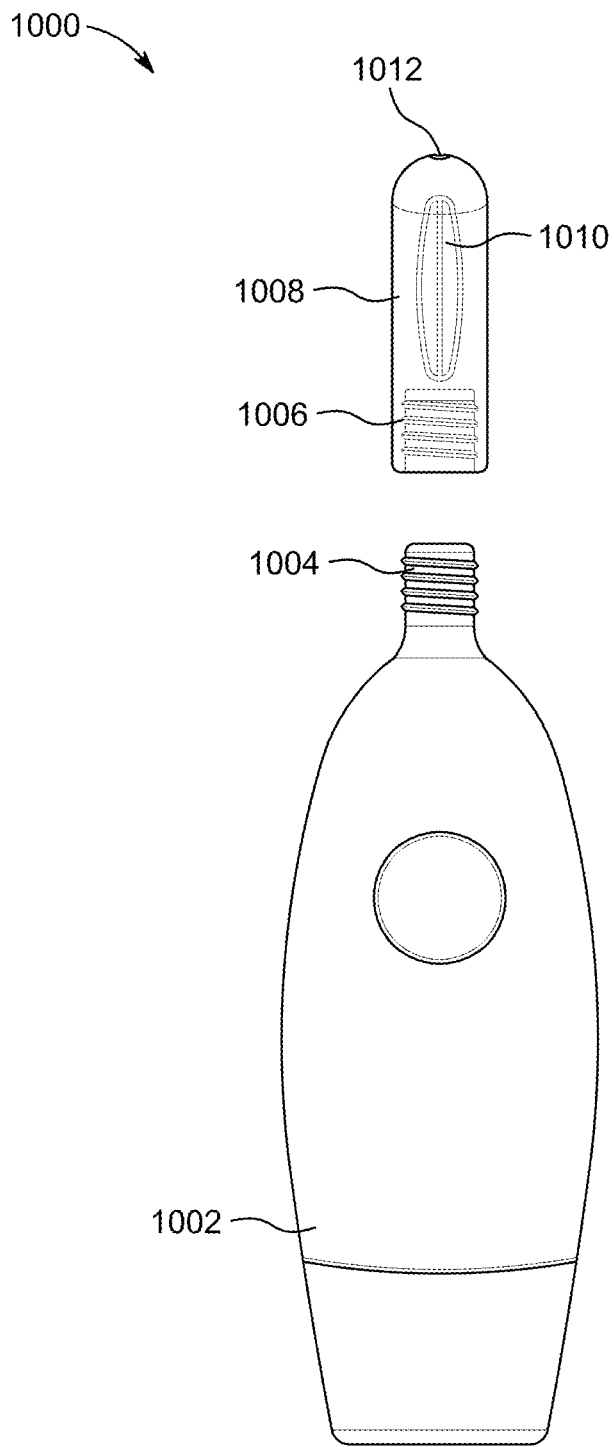
FIG. 10 shows an example single use intranasal drug delivery device according to some embodiments.

FIG. 10 shows an example single use intranasal drug delivery device 1000, pump 1002 incorporating a reservoir, a pump locking mechanism 1004, and compliant, soft nib 1008, with a nib locking mechanism 1006, shot chamber 1010 and spray tip 1012. In some embodiments the pump 1002 would be a spring actuated piston and the pump locking mechanism 1004 would lock with the nib locking mechanism 1006.

In some embodiments the device can include an olfactory marker that will be included with the excipient/drug that will provide biofeedback to the user. This may take the form of olfactory active marker that can signal to the user that the drug/excipient has been delivered to the olfactory region. This may include, but not be limited to markers which provide feedback of missed, un-deployed, deployed or over deployed drug/excipient. The marker can be included in the drug/excipient formulation or in some embodiments be added during the ejection process. In some embodiments, the marker may be included without the active drug agent to provide feedback to the user that an application and dosage (without the drug agent) was successful soliciting a psychological response.

Figure 11:
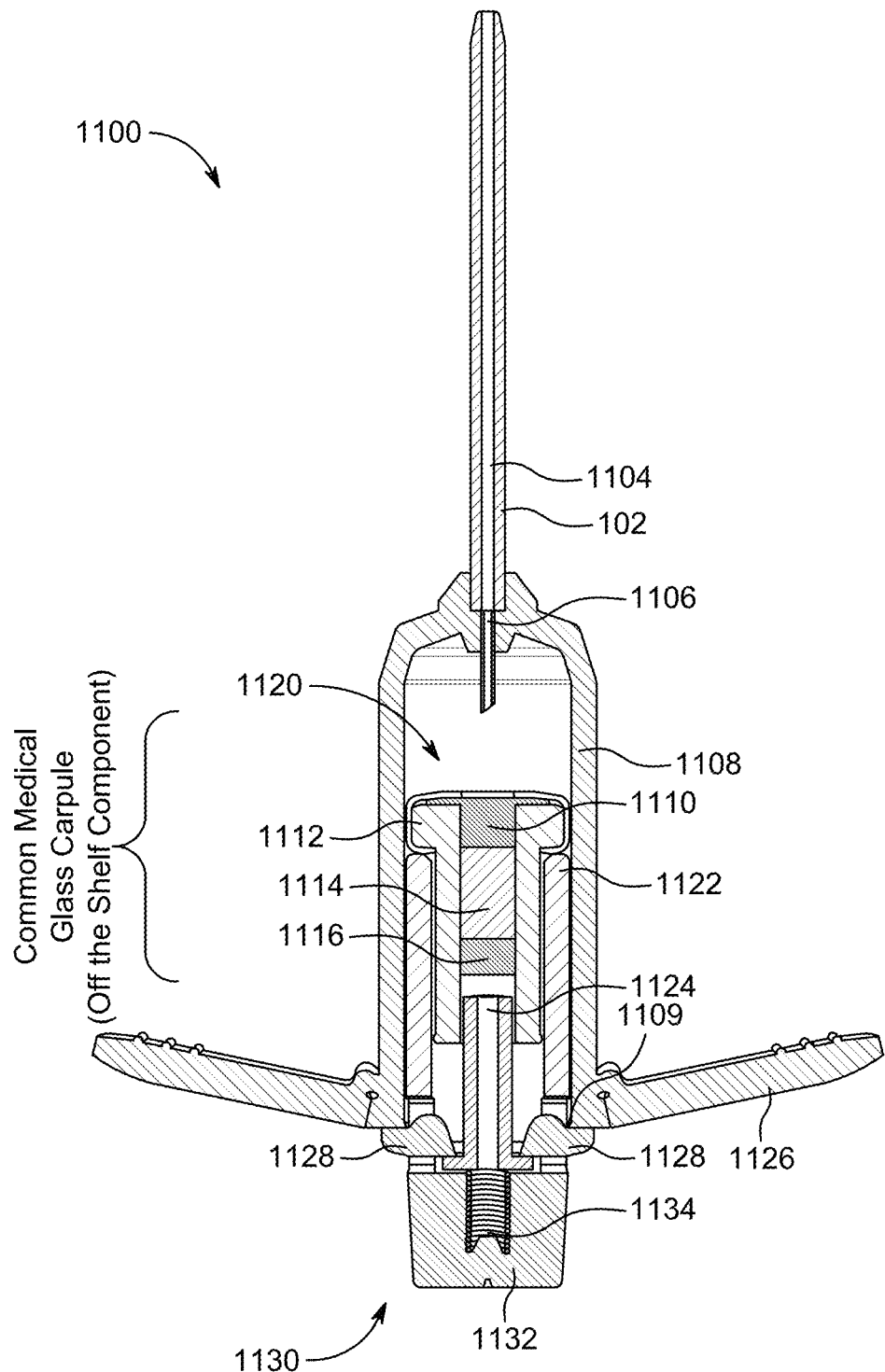
FIG. 11 shows an example intranasal drug delivery device according to some embodiments.

FIG. 11 shows an example intranasal drug delivery device 1100 according to some embodiments. The device 1100 comprises an outer chassis 1108 with a dispensing opening at a first end and an actuating opening at a second end. A dispensing tip is coupled to the dispensing opening, and an actuator 1130 is coupled to the actuating opening. As described below, fluid can be delivered to a nasal volume through the dispensing tip by pressing on the actuator 1130.

In some embodiments, the device 1100 is configured to receive a carpule 1120 (which comprises a diaphragm 1110, tube 1112, shot chamber 1114, and plunger 1116 as described below) pre-filled with a fluid, such as for example a pharmaceutical fluid. In the FIG. 11 example, the device 1100 comprises an enclosure 1122 slidably received within the outer chassis 1108 and shaped to accept a carpule 1120.

The carpule 1120 comprises a tube 1112 with an interior shot chamber 1114 that contains a fluid. In some embodiments, shot chamber 1114 may carry medication, such as ketamine of other pharmaceuticals, for delivery to a patient's nasal cavity or olfactory region. The shot chamber 1114 has a plunger 1116 on one end, and a diaphragm 1110 on the opposite end from the plunger 1116. The device 1100 is configured such that when a user engages the actuator 1130, the fluid in the shot chamber 1114 is delivered through the dispensing tip with predetermined flow characteristics. In the example illustrated in FIG. 11, the dispensing tip comprises a flexible cannula or nib 102 configured to deliver a laminar liquid slug, as described above.

In some embodiments, plunger 1116 may be engaged by a push rod 1124. In the FIG. 11 example, the push rod 1124 is located at the bottom of the enclosure 1112, and a spring 1134 is compressed between the push rod 1124 and a push button 1132. A locking mechanism 1128 holds the push rod 1124 and prevents it from engaging with plunger 1116 until the push button 1132 is pressed. In the illustrated example, the locking mechanism 1128 comprise a pair of pivotable tabs with inner ends engaging the push rod and outer ends extending past the outer edges of the enclosure 1122 such that when the enclosure 1122 is pushed into the chassis 1108 by pressing on the push button 1132 the tabs pivot to release the push rod 1124. In other embodiments, the locking mechanism may comprise one or more tabs of a lock material which is breakable by pressing on the push button 1132.

The diaphragm 1110 is puncturable by the needle 1106. Needle 1106 connects to channel 1104 in flexible nib 102, which may be inserted into the nasal cavity for fluid delivery as described above. When engaged, the fluid in shot chamber 1114 is forced through needle 1106 and channel 1104 into the nasal cavity. Arms 1126 may assist the user in gripping device 1100 and engaging push button 1132.

In some embodiments, to assemble device 1100, carpule 1120 may be inserted into the carpule enclosure 1122. The carpule enclosure 1122 may then be inserted into outer chassis 1108. In the illustrated example, the chassis 1108 comprises a resilient lip 1109 and the actuator opening deforms slightly to receive the carpule enclosure 1122 and carpule 1120, then holds them within the chassis 1108. In other embodiments, seals may be added to assist in detection of tampering.

Use of a carpule may be advantageous in certain situations because it is a commonly manufactured vessel for medication and may be made of a material that is non-reactive with medication, such as glass.

Figure 12:
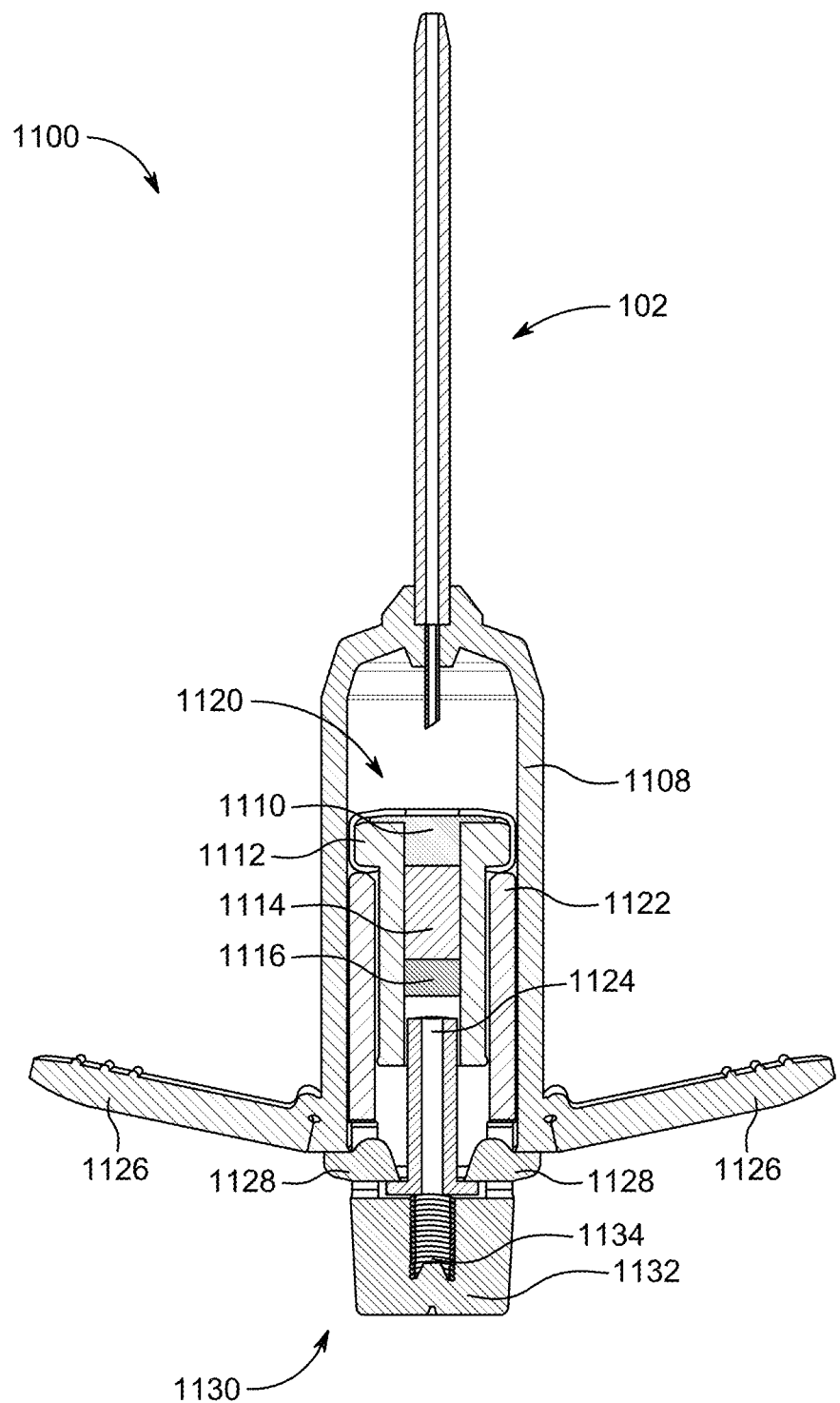
FIG. 12 shows an example intranasal drug delivery device according to some embodiments.

FIG. 12 shows an example intranasal drug delivery device 1100 according to some embodiments, wherein carpule 1120 is inserted in carpule enclosure 1122 and the carpule enclosure 1122 is inserted in outer chassis 1108, but the actuator 1130 has not been engaged by the user and locking mechanism 1128 holds push rod 1124 such that plunger 1116 is not engaged and fluid in shot chamber 1114 is not under pressure. Arms 1126 may be folded outward or inward against outer chassis 1108. The device 1100 may be stored without the fluid in shot chamber 1114 being under pressure. Flexible nib 102 may be placed in the nasal cavity of the patient prior to the actuator 1130 being engaged by the user.

Figure 13:
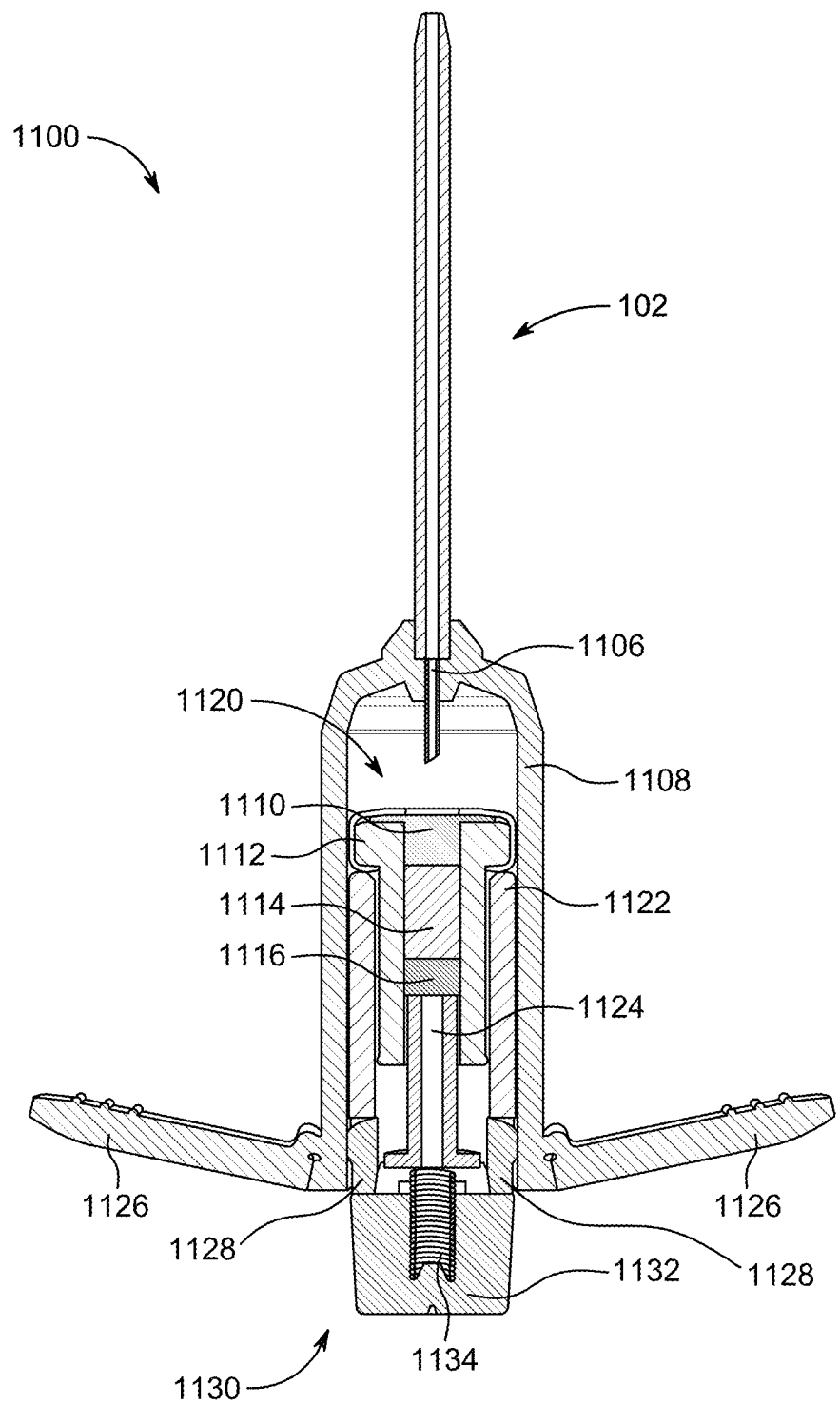
FIG. 13 shows an example intranasal drug delivery device according to some embodiments.

FIG. 13 shows an example intranasal drug delivery device 1100 according to some embodiments, wherein the user has engaged the push button 1132, for example, by pushing it with their thumb. The user may hold the device 1100 in their hand using arms 1126 in a folded out orientation. When user pushes the push button 1132, the locking mechanism 1128 releases push rod 1124. In some embodiments, the locking mechanism may comprise one or more tabs that break off to release push rod 1124, making the device 1100 useable only once. In other embodiments, the locking mechanism may comprise one or more tabs that fold or cantilever out of the way to release push rod 1124. When the locking mechanism 1128 is engaged it prevents the push rod 1124 from exerting pressure on the plunger 1116.

When the push rod 1124 presses against the plunger 1116 it puts the fluid in shot chamber 1114 under pressure, and will move the carpule 1120 toward the needle. In some embodiments, a spring 1134 may be included to such that the push rod 1124 exerts even pressure on plunger 1116, and once the locking mechanism 1128 is released the spring 1134 will cause carpule 1120 to move further into outer chassis 1108 toward needle 1106 until needle 1106 punctures diaphragm 1110. In some embodiments a user continues to push on the push button 1132 to move the carpule 1120 into outer chassis 1108 until the needle 1106 punctures diaphragm 1110.

In some embodiments, actuator 1130 may be a push button located at the bottom of device 1100, in other embodiments, actuator 1132 may be located on the side of outer chassis 1108.

In some embodiments, device 1100 may be designed for one-time use, with a locking mechanism 1128 comprising tabs that break off, or other sacrificial clips or structures such that carpule enclosure 1122 may not be removed from outer chassis 1118 to replace the spent carpule 1120 with a new carpule 1120 without the device 1100 being damaged.

Figure 14:
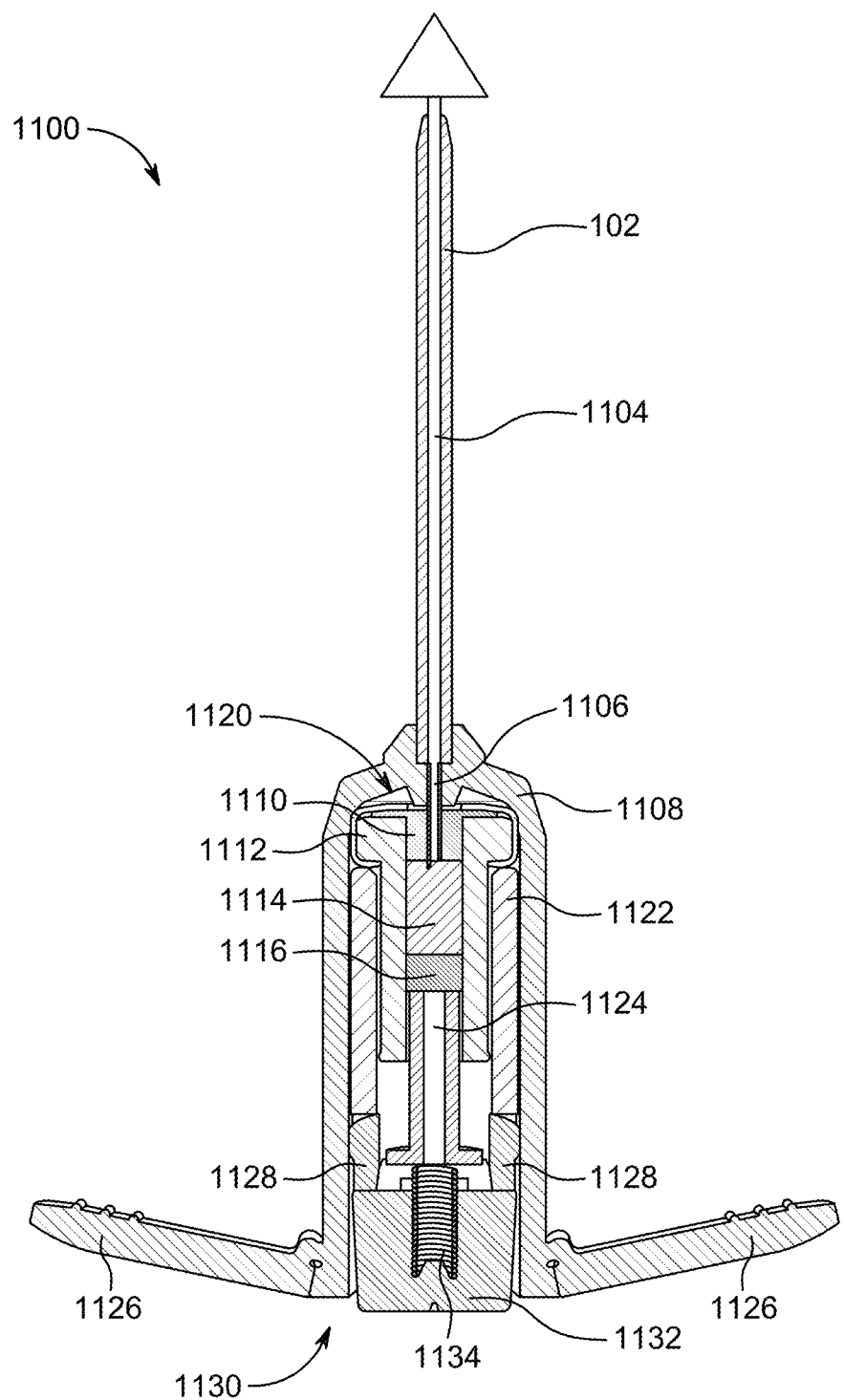
FIG. 14 shows an example intranasal drug delivery device according to some embodiments.

FIG. 14 shows an example intranasal drug delivery device 1100 according to some embodiments, wherein the user has pushed the actuator 1130 such that it causes the needle 1106 to puncture diaphragm 1110 so that the tip of needle 1106 is in contact with the fluid in shot chamber 1114. The fluid in shot chamber 1114 is under pressure from the plunger 1106 and may enter needle 1106 and flow through channel 1104 in nib 102. Fluid may flow through channel 1104 to be deposited in the nasal cavity or olfactory region of a patient.

Figure 15:
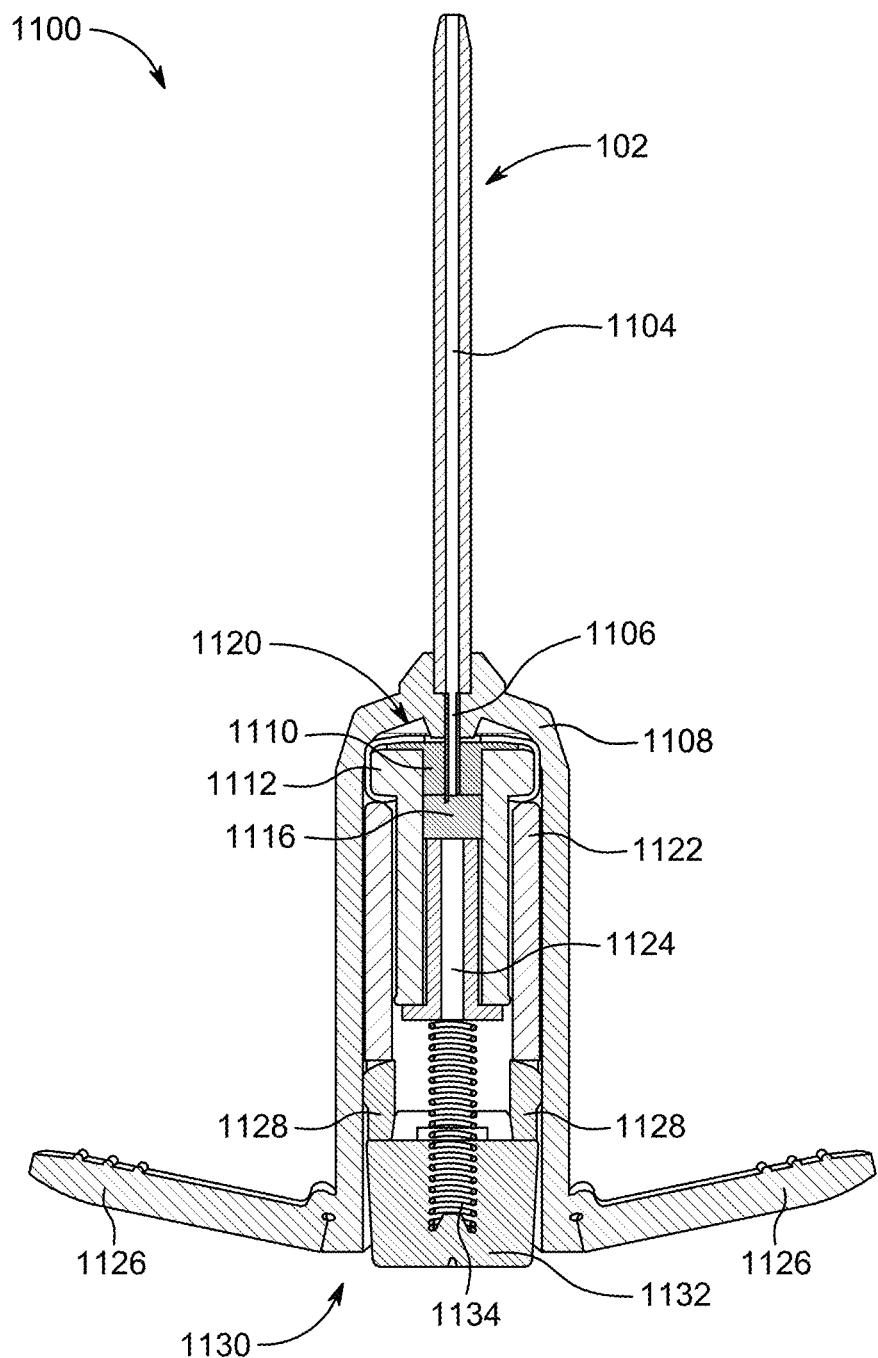
FIG. 15 shows an example intranasal drug delivery device according to some embodiments.

FIG. 15 shows an example intranasal drug delivery device 1100 according to some embodiments, wherein the user has pushed the actuator 1130 such that push rod 1124 has pushed plunger 1116 to reach diaphragm 1110, ending the ejection of fluid.

Figure 16:
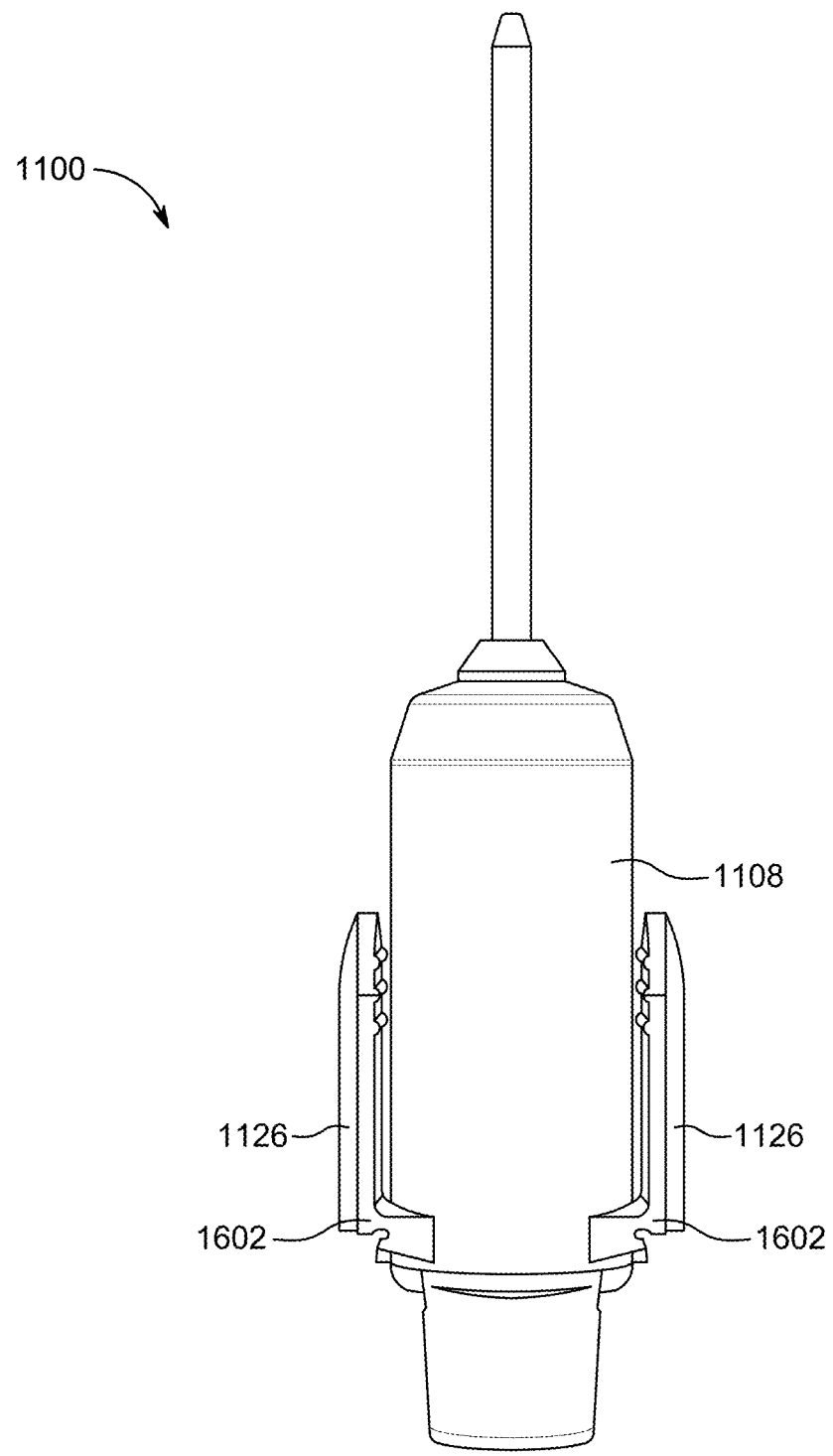
FIG. 16 shows an external view of an example intranasal drug delivery device according to some embodiments.

FIG. 16 shows an external view of an example intranasal drug delivery device 1100 according to some embodiments, wherein arms 1126 are hinged with hinge 1602 and may be folded against outer chassis 1108 for storage, packing and transport. Hinge 1602 may be a living hinge comprised of thin material, for example.

Figure 17:
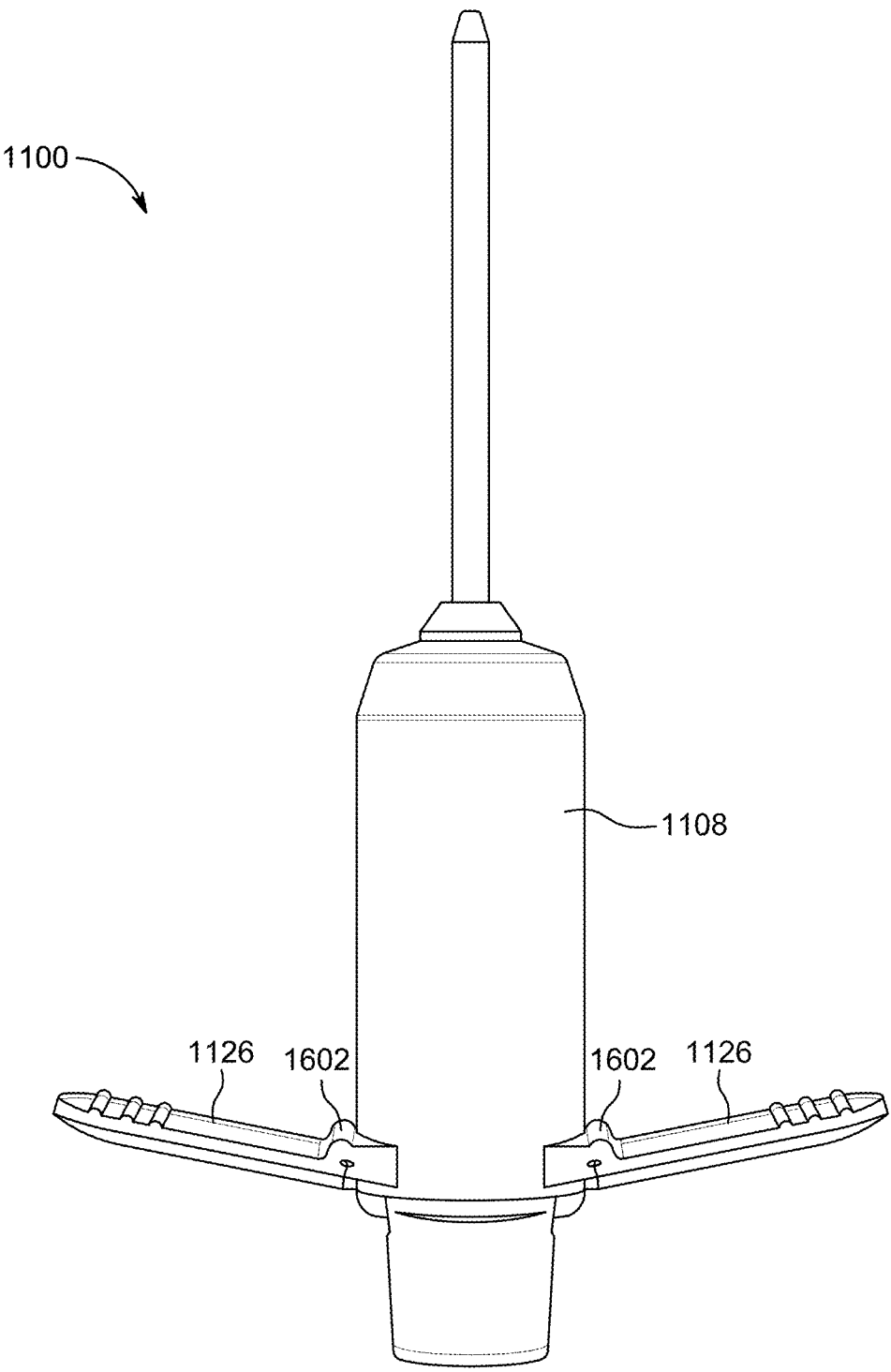
FIG. 17 shows an external view of an example intranasal drug delivery device according to some embodiments.

FIG. 17 shows an external view of an example intranasal drug delivery device 1100 according to some embodiments, wherein arms 1126 are folded outward from the outer chassis 1108, providing a grip for the user when using the device 1100. In the folded out position arms 1126 may provide a grip for a user wearing gloves or a user with dexterity challenges.

Figure 18:
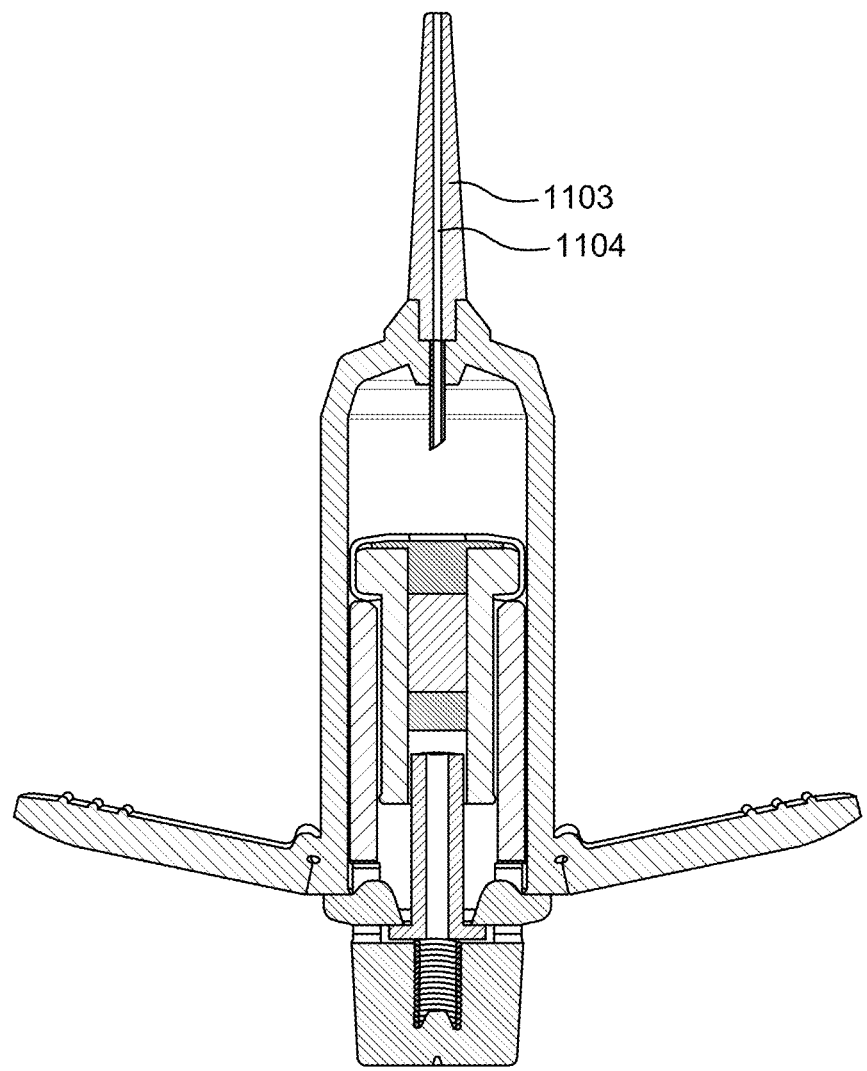
FIG. 18 shows an example intranasal drug delivery device according to some embodiments.

FIG. 18 shows an example intranasal drug delivery device 1100 according to some embodiments, wherein the dispensing tip comprises an atomizer 1103 designed to deliver a spray of fluid into the nasal cavity rather than a laminar liquid slug.

Figure 19A:
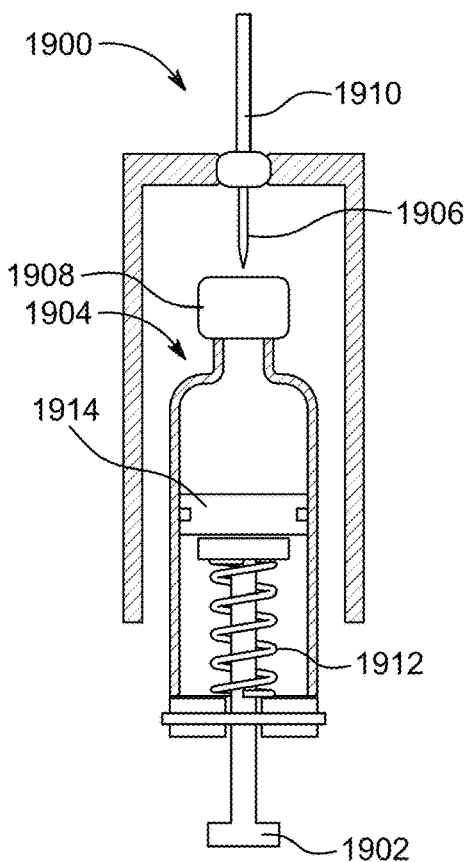
FIGS. 19 a-c show an example intranasal drug delivery device according to some embodiments.

FIGS. 19 a-c show an example intranasal drug delivery device 1900 according to some embodiments, wherein a two stage triggering mechanism is executed with a single button push.

Figure 19B:
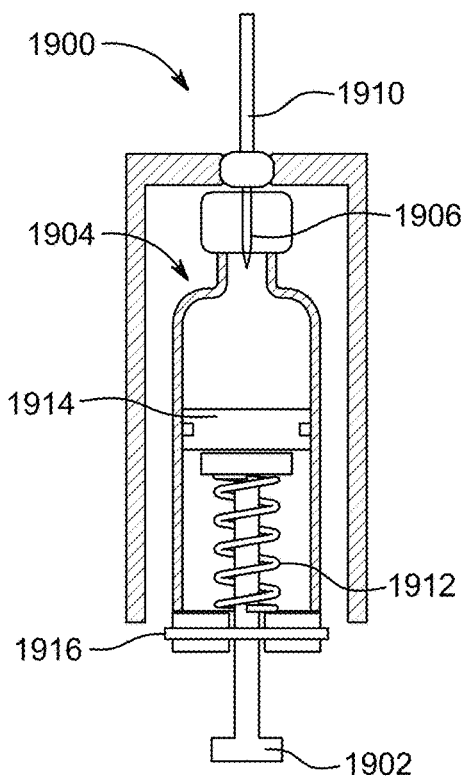

When actuator 1902 is first pushed by a user, the carpule 1904 is pressed into a needle 1906. The needle 1906 pierces the diaphragm 1908 (i.e. the carpule septum) and opens a fluid path through the channel 1910 (cannula) as shown in FIG. 19b. Actuator 1902 is connected directly to plunger 1914. When the actuator 1902 is pressed a second time by a user, spring 1912 releases and depresses the plunger 1914, ejecting fluid through the channel 1910 as shown in FIG. 19c.

Figure 19C:
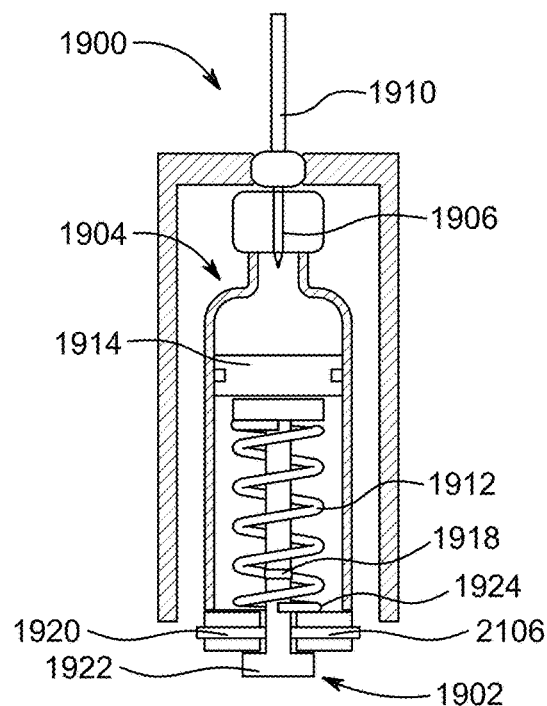

Spring 1912 may be released by breaking a shear pin 1916 into pieces 1918 and 1920, as shown in FIGS. 19b and 19c. In other embodiments the spring 1912 may be released when injection molded breakoff points or wings snap off of the plunger 1914. In other embodiments the spring 1912 may be released by a ball detent mechanism, molded snap fit component or other mechanism that is activated by reaching a pre-set force. In still other embodiments the spring 1912 may be released by the press force separating a magnet in the plunger from a magnet in the system body.

The travel of plunger 1914 is limited by a stop mechanism 1904 to set a total dose. Stop mechanism may comprise actuator projections 1922 that engage the base of the carpule 1924.

Figure 20A:
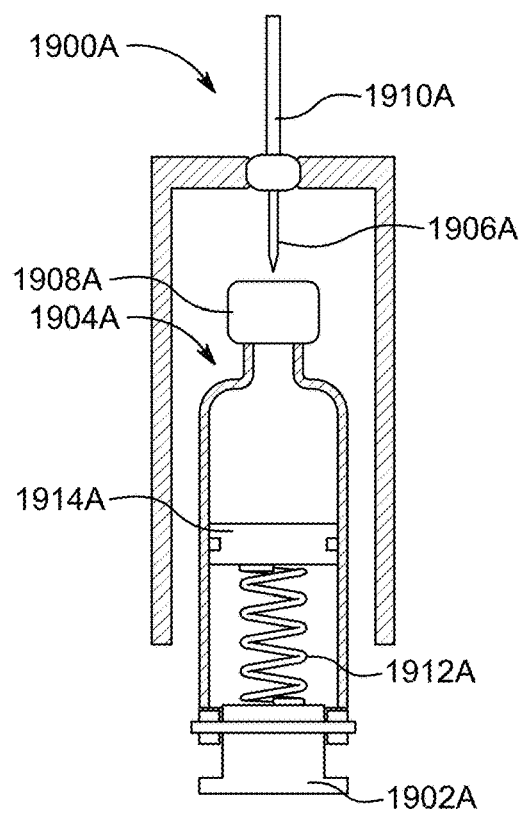
FIGS. 20 a-c show an example intranasal drug delivery device according to some embodiments.
Figure 20B:
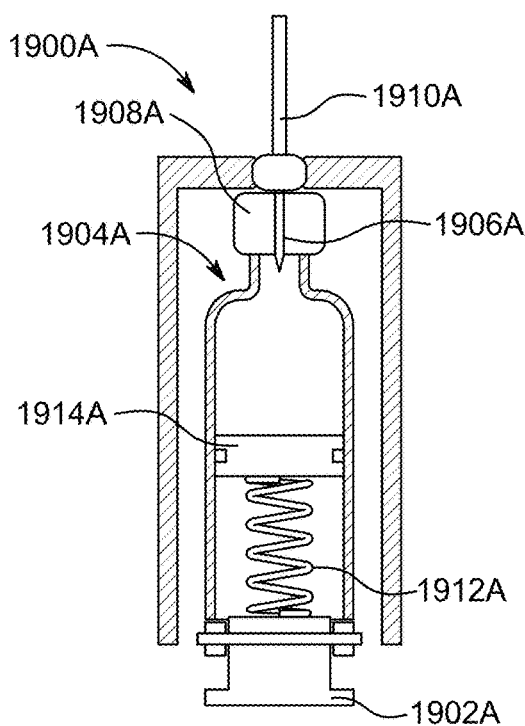
Figure 20C:
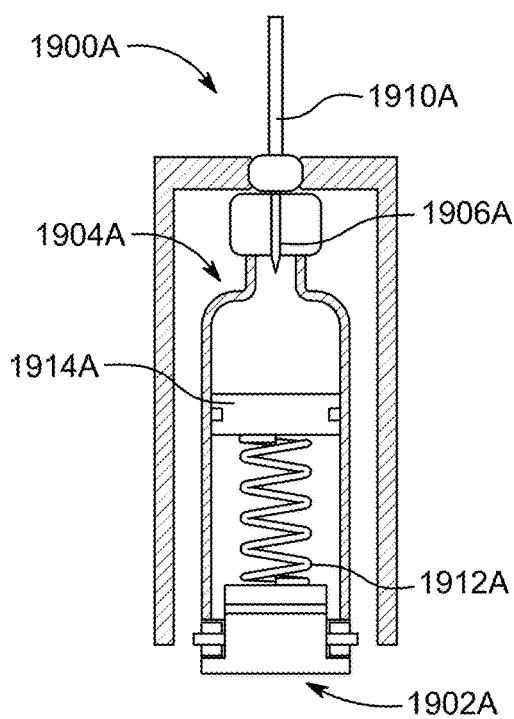

FIGS. 20 a-c show an example intranasal drug delivery device 1900A according to some embodiments, wherein a two stage triggering mechanism is executed with a single pushing motion. In this embodiment, the actuator 1902A is connected to spring 1912A, which is connected to plunger 1914A. After actuator 1902A is pushed by a user, the carpule 1904A is pressed into a needle 1906A and the needle 1906A pierces the diaphragm 1908A and opens a fluid path through the channel 1910A (cannula) as shown in FIG. 20b, a further press on the actuator 1902A builds up spring force in the user's hand (or other method used to press the button). When sufficient spring force is achieved, the actuator 1902A is released. The actuator 1902A may be released by several different methods, as described above. The spring force built up behind the actuator 1902A then rapidly compresses the spring 1912A between the actuator 1902A and the plunger 1914A. The spring 1912A then dispenses the fluid from the channel 1910A.

In some embodiments, the device comprises a dampening mechanism, examples of which are described further below with reference to FIGS. 21-33. Elements such as the dispensing tip, the needle that pierces the diaphragm, and an outer body are not shown in all views, but may be included in some embodiments. In each of these example embodiments, the device 2100/2200/2300/2400/2500/2600/2700/ 2800/2900/3000/3100/3200/3300 is configured to eject a jet of fluid through a channel with a controlled velocity profile. This assists in limiting shear on the delivered drug, some of which may be damaged by shear. For example, in some embodiments the device is configured to eject a jet of fluid starting at a high initial velocity but dropping linearly to a near zero jet velocity at the end of j et dispensing.

FIG. 21 shows an example device 2100 according to some embodiments, wherein a plunger 2102 is pushed by a spring 2104. In the FIG. 21 embodiment, the velocity of the plunger 2102 is controlled by an eddy current brake connected to the traveling end of the spring 2104. In the FIG. 21 embodiment, the dampening mechanism comprises a magnet 2106 connected to the plunger 2102 moves through a conductive jacket 2108, generating eddy currents and limiting the maximum plunger speed. In another embodiment the velocity of the plunger 2102 may be controlled by having magnet 2106 spun by a helix on a shaft connected to the traveling end of the spring (not shown).

FIG. 22 shows an example device 2200 according to some embodiments, wherein the velocity of the plunger 2202 travel is controlled by a dampening mechanism inherently formed by the construction of the device 2200 and the materials chosen. For example, in some embodiments part tolerances and material variations are controlled to provide a plunger 2202 friction and spring 2204 K value configured to ensure desired jet velocity profile.

FIG. 23 shows an example device 2300 according to some embodiments, wherein the velocity of the plunger 2302 is controlled by a dampening mechanism comprising a viscous dampener 2304 connected to the traveling end of the spring 2306. The dampener 2304 is filled with air or with viscous liquid (e.g. oil). The dampener 2304 controls the velocity of the traveling end of the spring 2306. Maximum velocity is limited by the dampener 2304, and as the spring 2306 extends, it's driving force decreases. This provides an initially high velocity followed by a decrease in velocity over the total dispensed volume.

Figure 24:
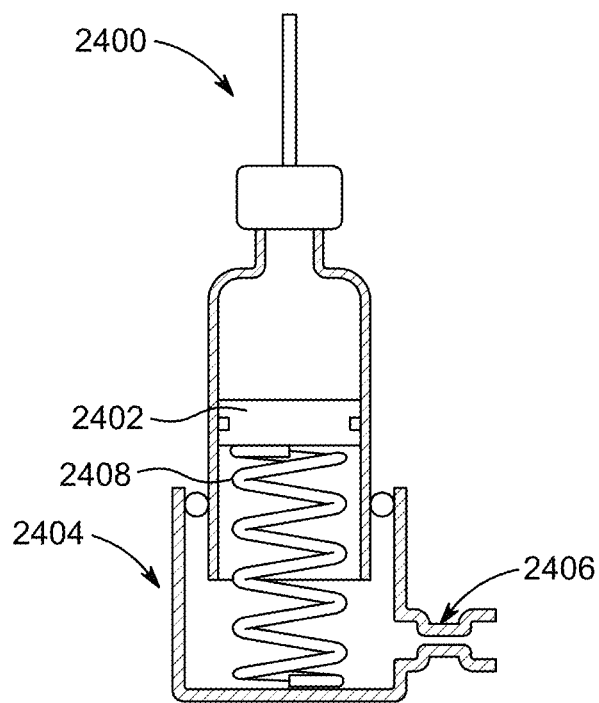
FIG. 24 shows an example intranasal drug delivery device according to some embodiments.

FIG. 24 shows an example device 2400 according to some embodiments, wherein the velocity of the plunger 2402 is controlled by a dampening mechanism comprising a sealed chamber 2404 attached to the back of the device 2400 connected to a spring 2408, which is connected to the plunger 2402. Air must be drawn into the chamber 2404 to allow the plunger 2402 to advance, but air flow into the chamber 2404 is limited by ether 1) a flow control valve (not shown) or 2) a simple flow restriction 2406 (e.g. narrow channel, orifice plate).

Figure 25:
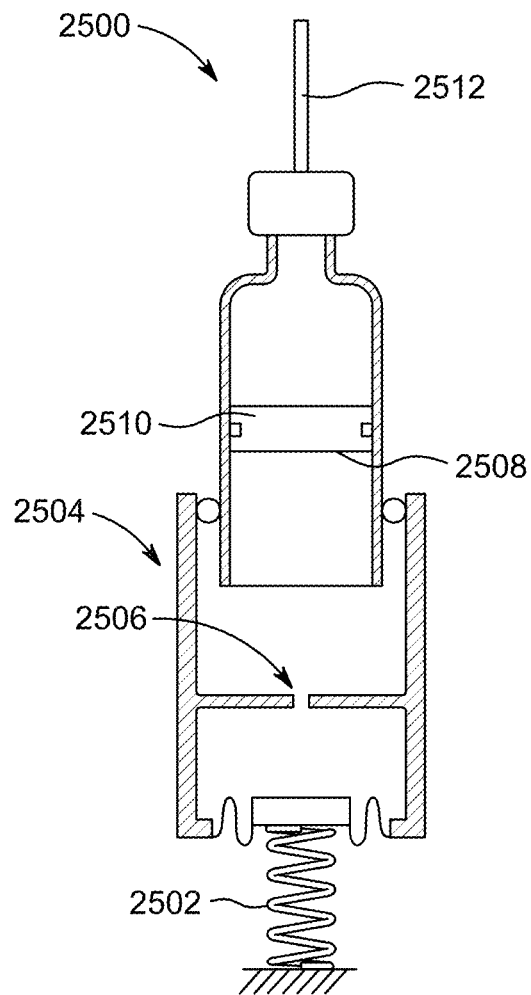
FIG. 25 shows an example intranasal drug delivery device according to some embodiments.

FIG. 25 shows an example device 2500 according to some embodiments, wherein the dampening mechanism comprises a spring 2502 used to compress a body of air (e.g. pushing on a bellows, pushing on a diaphragm, pushing a piston) into a sealed chamber 2504. The compressed air flow through a flow restriction 2506 that controls air flow rate to the device 2500. The outside of the device 2500 body seals to the sealed chamber 2504 (e.g. O-ring seal). The air then pushes on the back side 2508 of the piston 2510, pushing the drug out of the channel 2512. Because the flow rate of air is controlled by the flow restriction 2506, the rate of travel for the piston 2510 is controlled. The flow restriction 2506 may be simple, like an orifice plate, narrow tube, or narrow drilled hole, but it may also be a pneumatic device like a pressure relief valve, or flow control valve.

Figure 26A:
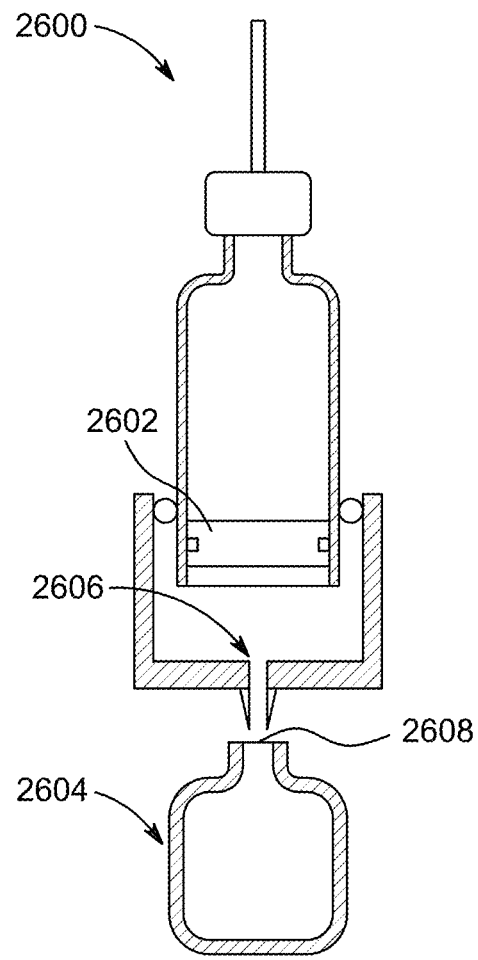
FIGS. 26 a-b show an example intranasal drug delivery device according to some embodiments.
Figure 26B:
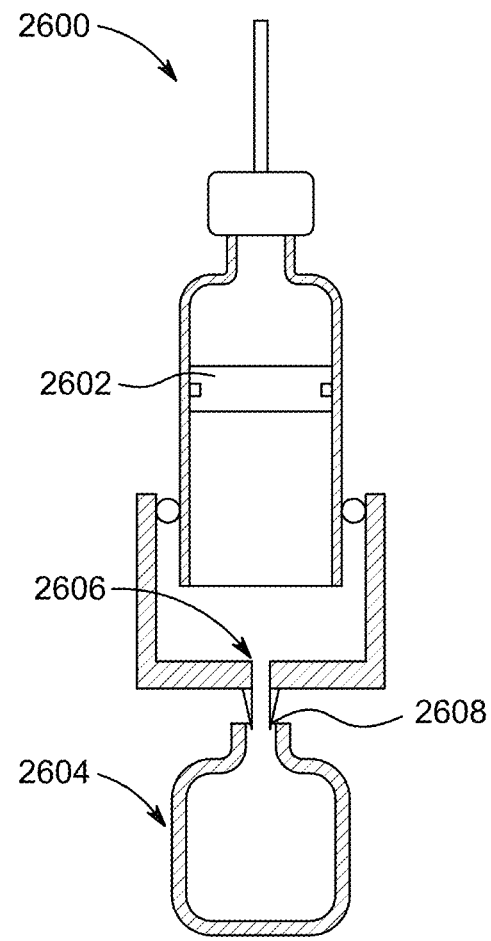

FIGS. 26 *a-b* show an example device 2600 according to some embodiments, wherein control over the velocity of the plunger 2602 is be achieved by a dampening mechanism comprising a container 2604 of compressed gas (e.g. CO2 canister, sealed canister of air, N2, etc.). The container 2604 of compressed gas is connected to the flow restriction 2606 by piercing a membrane 2608 or septum or by connecting with a valve. A leak point may be added to the chamber to cause pressure applied to the device 2600 to dissipate over time. This provides a decreasing velocity profile for the fluid jet. The compressed gas container may be connected to the device 2600 chamber by piercing a membrane on the canister, by a valve, or by a similar mechanism.

Figure 27A:
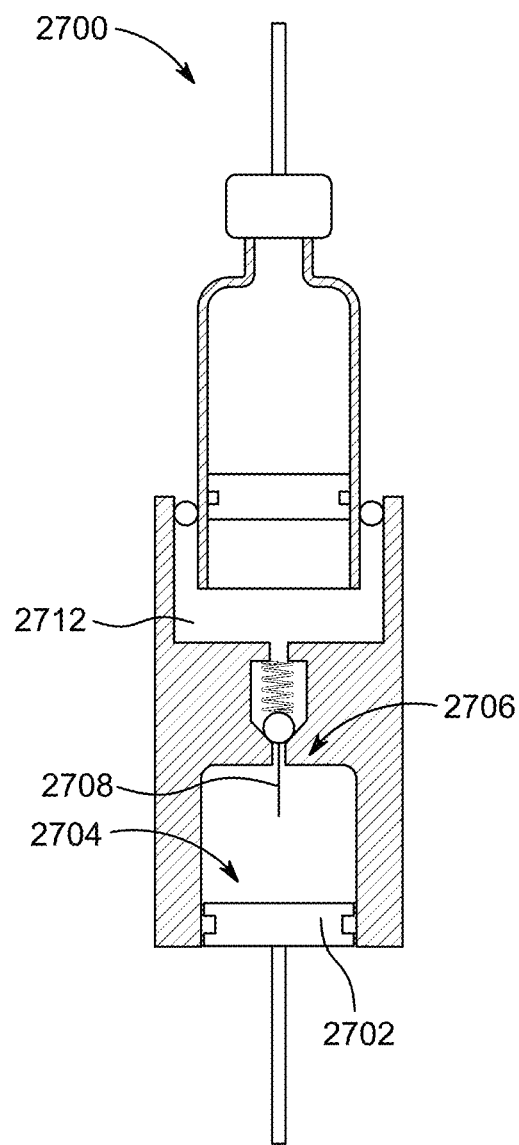
FIGS. 27 a-b show an example intranasal drug delivery device according to some embodiments.
Figure 27B:
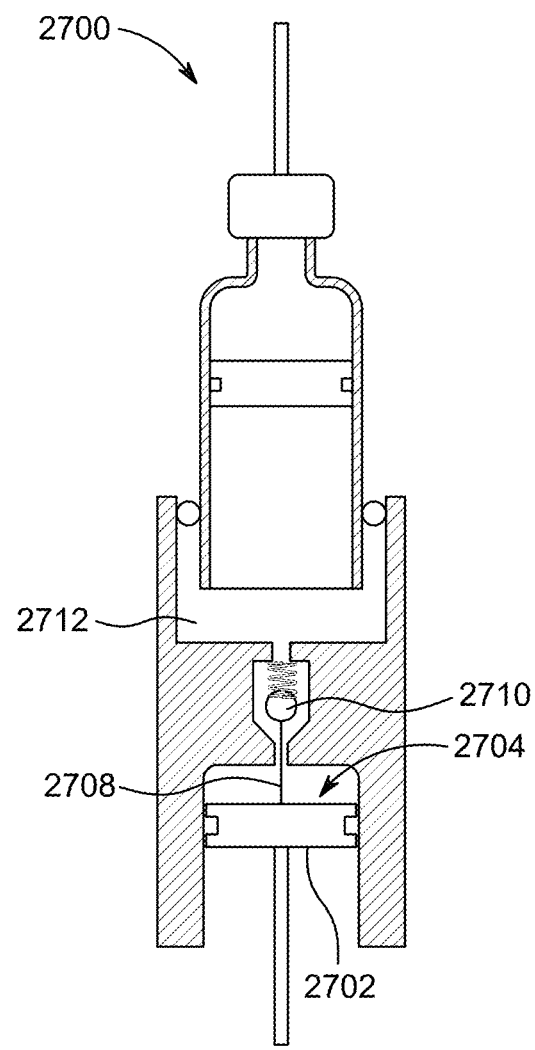

FIGS. 27 *a-b* show an example device 2700 according to some embodiments, wherein the dampening mechanism comprises a piston 2702, sealed chamber 2704, pin and ball valve 2706. In this embodiment, the piston 2702 is moved and compressed gas in sealed chamber 2704 is provided instantaneously using a mechanically operated valve such as pin and ball valve 2706. When the piston 2702 reaches the top of the chamber 2704, a pin 2708 is pushed by the piston 2702, opening a ball valve 2710 to release pressure into the shot chamber 2712.

FIG. 28 shows an example device 2800 according to some embodiments, wherein a plunger 2802 is pushed by an electric motor 2804 (e.g. stepper motor, DC motor, brushless motor, etc.) which provides the function of both actuating force and a dampening mechanism. Circuitry onboard the electric motor 2804 controls the plunger 2802 velocity to set the desired ejected fluid velocity profile. Control of the electric motor 2804 may be open loop or closed loop. Motor 2804 may be a liner motor, or a rotary motor combined with gearing, a linkage, cam, lead screw, or other mechanical element to drive the plunger 2802.

FIGS. 29 *a-c* show an example device 2900 according to some embodiments, wherein controlled jet velocity is provided by a dampening mechanism comprising an elastomeric chamber 2902. This occurs in two steps. First, the plunger 2904 is depressed to fill the elastomeric chamber 2902, as shown in FIG. 29*b*. Second the fluid path to the channel 2906 is opened, now spring force stored in the stretched elastomeric chamber 2902 forces the fluid out of the channel 2906 as shown in FIG. 29*c*.

The flow resistance of the fluid path out of the elastomeric chamber 2902 is matched to the stiffness of the elastomeric chamber 2902 to provide a controlled jet velocity profile. As the elastomeric chamber 2902 relaxes, the pressure on the fluid decreases, so this provides an initial high velocity followed by a decrease in jet velocity.

Figure 30A:
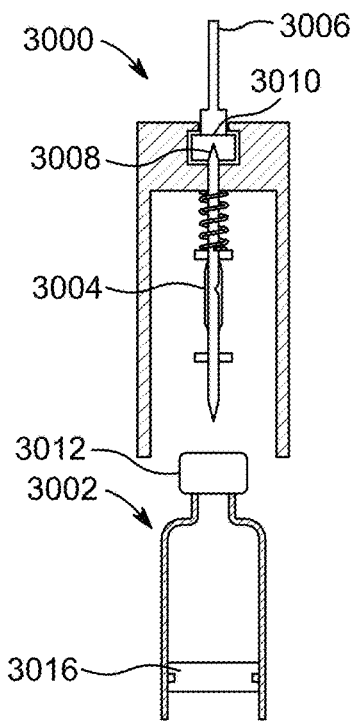
FIGS. 30 a-c show an example intranasal drug delivery device according to some embodiments.
Figure 30B:
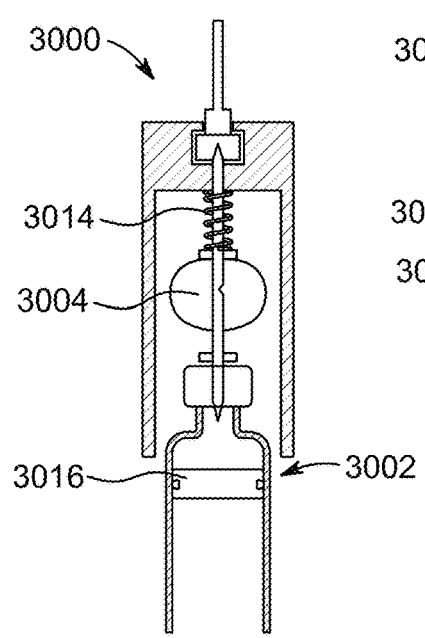
Figure 30C:
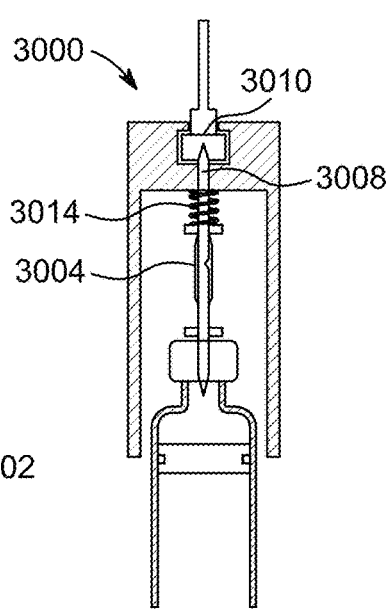

FIGS. 30 *a-c* show an example device 3000 according to some embodiments, wherein a carpule 3002 is depressed to fill the elastomeric chamber 3004 and the fluid path to channel 3006 is opened with a single motion. In this embodiment, a needle 3008 is partially embedded in a septum 3010 to seal the end of the needle 3008, as shown in FIG. 30*a*. First, as the plunger 3016 moves, the diaphragm 3012 is pierced. As the plunger 3016 continues to move as shown in FIG. 30b, the elastomeric chamber 3004 is loaded with fluid. The spring 3014 prevents travel of the carpule 3003 until the plunger 3016 is sufficiently depressed. Third, the plunger 3016 travel ends, the spring 3014 is compressed, and the septum 3010 is pierced by needle 3008 as shown in FIG. 30c. Fourth, the elastomeric chamber 3004 forces fluid out through the channel 3006. As the elastic elastomeric chamber 3004, pressure drops, providing a decreasing velocity profile. Chamber geometry can be varied to make a linear or non-linear decreasing velocity profile.

Figure 31:
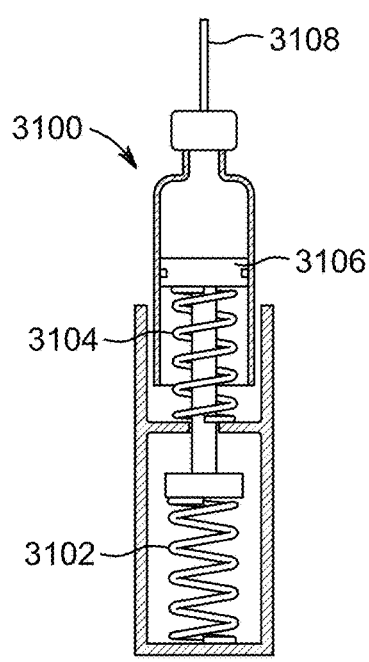
FIG. 31 shows an example intranasal drug delivery device according to some embodiments.

FIG. 31 shows an example device 3100 according to some embodiments, wherein a large spring 3102 with a limited initial travel is used to break static friction in the piston 3106 and a second spring 3104 provides the force to fully dispense the drug. Large spring 3102 is a higher force spring than second spring 3104. The flow path out of the channel 3108 is long enough that the high velocity travel from the large spring 3102 does not cause fluid to leave the channel 3108.

Figure 32:
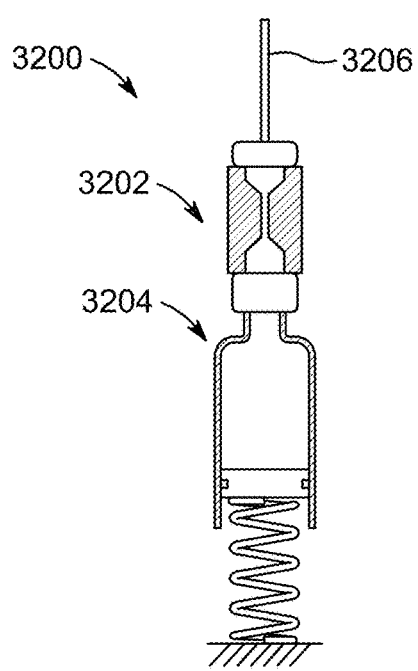
FIG. 32 shows an example intranasal drug delivery device according to some embodiments.

FIG. 32 shows an example device 3200 according to some embodiments, wherein the flow rate of the jet is controlled by a flow restriction device 3202 between a carpule 3204 and a channel 3206. The flow restriction device 3202 can be long and gradual to keep a laminar flow profile. This will prevent excessive shear on the delivered drug (e.g. protecting the viability of vaccines). The flow restriction device 3202 could also be more compact but producing a turbulent flow. This would make a more compact device suitable for delivering robust therapeutic agents. The flow restriction device 3202 could also be replaced by an active element like a constant velocity flow control valve, a pressure relief valve, or a pressure control valve.

Figure 33A:
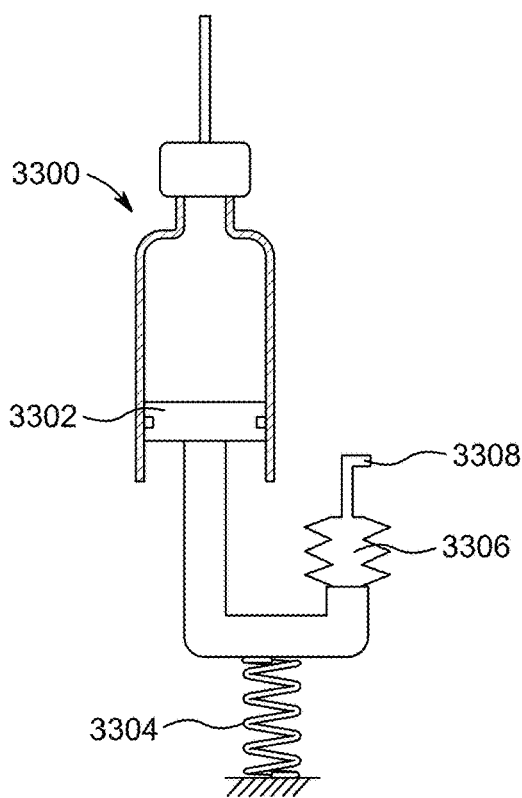
FIGS. 33 a-c show an example intranasal drug delivery device according to some embodiments.
Figure 33B:
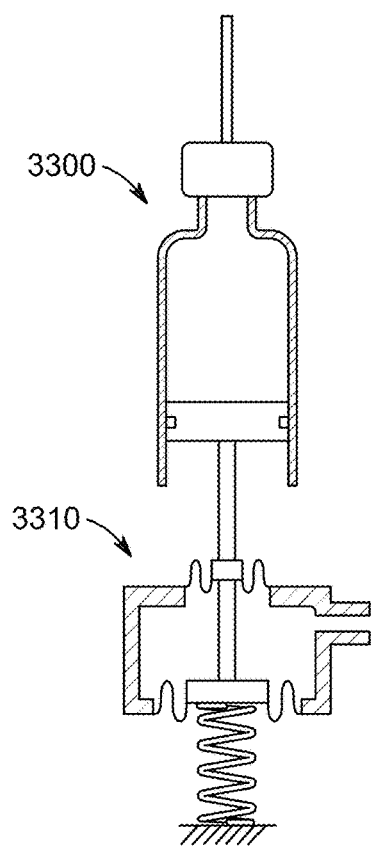
Figure 33C:
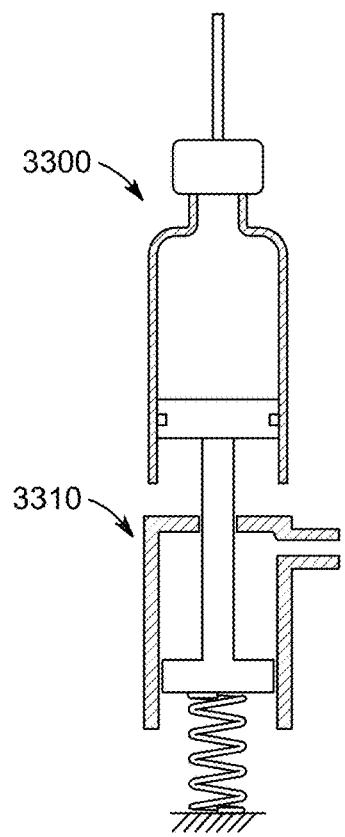

FIG. 33 a-c show an example device 3300 according to some embodiments, wherein the plunger 3302 is driven by a spring 3304, but piston velocity is controlled by bellows 3306 filled with air. As the piston 3302 travels up, the bellows 3306 are compressed, and air is forced through a flow restriction 3308 (e.g. simple orifice plate, small drilled hole, pressure control valve, flow rate control valve). The rate that the bellows 3306 can deform is controlled by the rate of air flow through the flow restriction 3308. This could be accomplished by an arrangement where air is contained in a diaphragm 3310, rolling diaphragm or a piston as shown in FIGS. 33b and 33c. It may also be accomplished in the same configuration shown in FIG. 33a but with a diaphragm, rolling diaphragm, or piston.

Air may vent externally to the device, or it may vent into a secondary chamber to avoid the need for an external vent.

Figure 36:
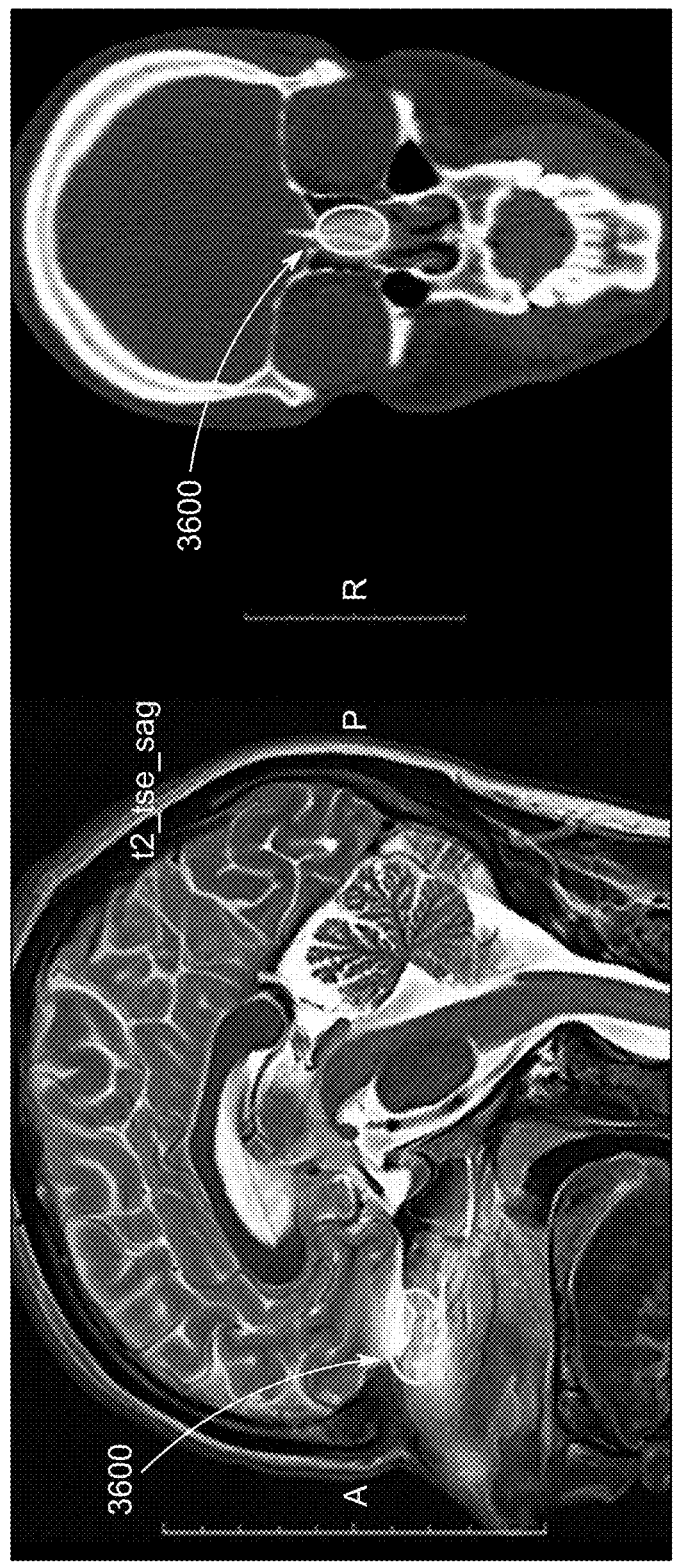
FIG. 36 shows images from a scan of a test subject during testing of a prototype device with a tracer fluid.

A prototype device including a cannula and dampening mechanism has been tested to demonstrate targeted delivery of the fluid bolus. The testing comprised inserting the cannula into the upper nares of a patient and ejecting a laminar flow of fluid through the cannula. In the testing, technicium 99 was used as a tracer fluid. A scan of the patient performed following the injection of the laminar flow of fluid show that the fluid is deposited at the olfactory region of the patient 3600, as shown in FIG. 36. The presence of the technicium 99 appears as a light region on the scan shown in FIG. 36.

The foregoing discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements.

Although the embodiments have been described in detail, it should be understood that various changes, substitutions and alterations can be made herein.

Moreover, the scope of the present application is not intended to be limited to the particular embodiments of the process, machine, manufacture, composition of matter, means, methods and steps described in the specification.

As can be understood, the examples described above and illustrated are intended to be exemplary only.

What is claimed is:

1. An intranasal fluid delivery device comprising:
   (a) a compliant dispensing tip for dispensing a fluid, the compliant dispensing tip coupled to a hollow needle;
   (b) a shot chamber for containing the fluid, the shot chamber comprising a diaphragm disposed at a first end and a plunger disposed at a second end; and
   (c) an actuator operatively coupled to a push rod moveable toward the second end of the shot chamber, wherein upon the actuator being engaged, the actuator allows the push rod to push against the plunger, causing the shot chamber to move toward the needle such that the needle punctures the diaphragm, the plunger then exerting pressure on the fluid in the shot chamber such that the fluid flows out of the needle into the compliant dispensing tip;

wherein the compliant dispensing tip comprises: a compliant and flexible soft nib; and a nostril stop that is configured to: (I) limit depth of insertion of the compliant and flexible soft nib into a nasal cavity of a user or patient; and (II) provide feedback to the user when the compliant and flexible soft nib reaches a location proximate to an olfactory region in the nasal cavity of the user or patient, wherein the compliant and flexible soft nib defines a channel therein for dispensing the fluid therefrom as a laminar flow and wherein: (i) the compliant and flexible soft nib is configured to conform with a nasal cavity of the user or patient and follows the septum of the user or patient and accommodates nasal cavity anatomy differences of the user or patient while being self-guided through an internal nasal geometry of the user or patient to a location proximate to an olfactory region in the user's or patient's nasal cavity; (ii) the nostril stop is configured to provide the feedback to the user that the compliant and flexible soft nib has reached a location proximate to an olfactory region in the user's or patient's nasal cavity; and (iii) the compliant and flexible soft nib (A) is configured to stop at the position proximate to the olfactory region in the user's or patient's nasal cavity and (B) is configured to precisely deliver the fluid to the olfactory region of the user or patient from the position proximate to the olfactory region in the user's or patient's nasal cavity.

2. The intranasal fluid delivery device of claim 1, wherein the actuator comprises a locking mechanism, and wherein user engagement of the actuator releases the locking mechanism, allowing the push rod to push against the plunger, further wherein the locking mechanism comprises one or both of:
   a) one or more tabs comprising a lock material, configured such that the locking mechanism is released by the user breaking the lock material; and
   b) one or more pivotable tabs, configured such that the locking mechanism is released by the user pivoting the pivotable tabs.

3. The intranasal fluid delivery device of claim 2, further comprising a spring in alignment with the push rod, wherein the locking mechanism is configured to maintain the spring under a pressure condition, wherein releasing the locking mechanism releases the spring from the pressure condition, causing the push rod to push against the plunger.

4. The intranasal fluid delivery device of claim 3, further comprising a cocking mechanism configured to be activated by the user, wherein the intranasal fluid delivery device is configured such that when the user activates the cocking mechanism, pressure is applied to the spring and the spring is thereby placed under the pressure condition.

5. The intranasal fluid delivery device of claim 1, comprising a cartridge configured for containing, or containing, the fluid, wherein the cartridge comprises the shot chamber, the diaphragm, and the plunger.

6. The intranasal fluid delivery device of claim 5, wherein the cartridge is a removable and replaceable component of the intranasal fluid delivery device.

7. The intranasal fluid delivery device of claim 1, further comprising a housing, chassis or outer body.

8. The intranasal fluid delivery device of claim 7, wherein the housing, chassis or outer body is configured: (a) to be removable in whole or in part from other components of the intranasal fluid delivery device; (b) to allow for the user to gain access to a cartridge configured for containing, or containing, the fluid, or (c) a combination thereof.

9. The intranasal fluid delivery device of claim 1, further comprising a stopping mechanism configured to limit a travel distance of the push rod.

10. The intranasal fluid delivery device of claim 1, further comprising a dampening mechanism configured to generate a controlled velocity profile of the fluid dispensed from the compliant dispensing tip, and wherein the dampening mechanism comprises at least one of a magnet, a spring, a viscous dampener, a sealed chamber with an airflow restriction, a container of compressed gas, a valve, a motor, an elastomeric chamber, and a flow restriction device.

11. The intranasal fluid delivery device of claim 1, further configured such that, upon the needle puncturing the diaphragm the shot chamber then bottoms out and the plunger then exerts pressure on the fluid in the shot chamber such that the fluid flows out of the needle into the compliant dispensing tip.

12. The intranasal fluid delivery device of claim 1, wherein the compliant dispensing tip, and the compliant and flexible nib, complies with the internal nasal geometry of the user or patient to guide a delivery end of the compliant dispensing tip proximate to the olfactory region in the user's or patient's nasal cavity.

* * * * *